United States Patent [19]

Jones et al.

[11] Patent Number: 4,837,234
[45] Date of Patent: Jun. 6, 1989

[54] PROSTAGLANDINS

[75] Inventors: Robert L. Jones; Norman H. Wilson, both of Edinburgh, Scotland

[73] Assignee: National Research Development Corporation, London, England

[21] Appl. No.: 869,735

[22] Filed: Jul. 22, 1986

Related U.S. Application Data

[62] Division of Ser. No. 531,899, Aug. 23, 1983, Pat. No. 4,628,061.

[30] Foreign Application Priority Data

Dec. 23, 1981 [GB] United Kingdom ............... 8138715
Dec. 10, 1982 [WO] PCT Int'l Appl. .... PCT/GB82/00348

[51] Int. Cl.$^4$ ............... C07D 177/00; A61K 31/557
[52] U.S. Cl. ............................ 514/469; 514/529;
514/530; 514/542; 514/562; 514/564; 514/565;
546/269; 546/305; 546/306; 546/309; 549/463;
560/16; 560/34; 560/118; 560/120; 562/427;
562/439; 562/500; 562/502; 564/17; 564/57;
564/180
[58] Field of Search ............... 560/118, 120, 16, 34;
562/500, 502, 427, 439; 564/17, 57, 180;
549/463; 546/269, 305, 306, 309; 514/469, 524,
530, 542, 562, 564, 565

[56] References Cited

U.S. PATENT DOCUMENTS

| | | | |
|---|---|---|---|
| 4,073,933 | 2/1978 | Shimomura | 549/463 |
| 4,416,896 | 11/1983 | Nakane | 549/463 |
| 4,418,076 | 11/1983 | Nakane | 549/463 |
| 4,456,615 | 6/1984 | Nakane | 549/463 |
| 4,463,015 | 7/1984 | Haslanger | 549/463 |
| 4,537,904 | 8/1985 | Suitman | 549/463 |
| 4,537,981 | 8/1985 | Suitman | 549/463 |
| 4,556,675 | 12/1985 | Suitman | 549/463 |
| 4,614,825 | 9/1986 | Suitman | 549/463 |

FOREIGN PATENT DOCUMENTS

| | | | |
|---|---|---|---|
| 0044711 | 1/1982 | European Pat. Off. | 549/463 |
| 1353922 | 9/1974 | United Kingdom | 549/463 |
| 1583146 | 1/1981 | United Kingdom | 549/463 |
| 2075503 | 4/1981 | United Kingdom | 549/463 |
| 2081258 | 2/1982 | United Kingdom | 560/120 |

Primary Examiner—Robert Gerstl
Attorney, Agent, or Firm—Oblon, Fisher, Spivak, McClelland & Maier

[57] ABSTRACT

Novel compounds have a formula (I)

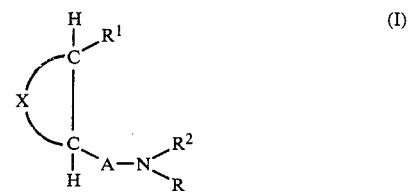

wherein

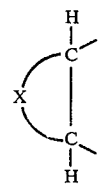

represents a bicyclo [2,2,1] hept-2Z-ene, bicyclo [2,2,1] heptane, 7-oxa-bicyclo [2,2,1] hept-2Z-ene, 7-oxa-bicyclo [2,2,1] heptane, bicyclo [2,2,2] oct-2Z-ene or bicyclo [2,2,2] octane substituted at the 5-position by the group $R^1$ and at the 6-position by the group $ANR^2R$, a 6,6-dimethyl-bicyclo [3,1,1] heptane substituted at the 2-position by the group $R^1$ and at the 3-position by the group $ANR^2R$ or at the 2-position by the group $ANR^2R$ and at the 3-position by the group $R^1$, a cyclohex-1-ene or cyclohexane substituted at the 4-position by the group $R^1$ and at the 5-position by the group $ANR^2R$ or a 1-hydroxycyclopentane substituted at the 2-position by the group $R^1$ and at the 2-position by the group $ANR^2R$, $R^1$ is a 6-carboxyhex-2-enyl group or a modification thereof as defined herein; A is an unbranched or branched aliphatic hydrocarbon group with a chain length between the points of attachment to the divalent cyclic group and to the group $NR^2R$ of 1 to 5 carbon atoms or such a group substituted by an aromatic group; $R^2$ is hydrogen, an aliphatic hydrocarbon group, an aromatic group or an aliphatic hydrocarbon group substituted by an aromatic group or groups; and R is a group $-CO.NR^3R^4$, $-CS.NR^3R^4$, $-CNH.NR^3R^4$, $-CO.R^4$ or $-CS.R^4$ in which $R^3$ is hydrogen, an aliphatic hydrocarbon group, an aromatic group or an aliphatic hydrocarbon group substituted by an aromatic group or groups, and $R^4$ is an aliphatic hydrocarbon group, an aromatic group or an aliphatic hydrocarbon group substituted directly by an aromatic group or groups and/or through an oxygen or sulphur atom either by an aromatic group or by an aliphatic hydrocarbon group substituted directly by an aromatic group or groups. The compounds are of value for use in pharmaceutical compositions particularly in the context of the inhibition of thromboxane activity.

36 Claims, No Drawings

PROSTAGLANDINS

This is a division of application Ser. No. 531,899, filed Aug. 23, 1983, now U.S. Pat. No. 4,628,061.

BACKGROUND OF THE INVENTION

1. Field of the Invention:

This invention relates to biologically active compounds and in particular to certain novel compounds exhibiting activity at thromboxane receptor sites.

2. Discussion of the Background

Thromboxane $A_2$ ($TXA_2$), which is derived from arachidonic acid via prostaglandin $H_2$ ($PGH_2$), is implicated in several potentially noxious actions on various body systems, including platelet aggregation, bronchoconstriction and pulmonary and systemic vasoconstriction. Thus $TXA_2$ may be involved in the normal sealing of blood vessels following injury but in addition may contribute to pathological intravascular clotting or thrombosis. Moreover, the constrictor actions of $TXA_2$ on bronchiolar, pulmonary vascular and systemic vascular smooth muscle may be important in the development of several anaphylactic conditions including bronchial asthma. There is also some evidence to implicate $PGH_2$ and $TXA_2$ in the genesis of inflammation.

Compounds having activity at thromboxane receptor sites, and most especially compounds which are inhibitors of thromboxane activity, are therefore of interest in one or more areas of medical treatment including the treatment of thrombotic disorders, the treatment of anaphylactic disease states, and treatments utilising anti-inflammatory agents. Compounds of this type are described and claimed in co-pending UK patent applications Nos. 8000278 and 8000279 (published as GB No. 2039480A and GB No. 2039909A, respectively) and in corresponding applications filed elsewhere, and also in co-pending UK patent application No. 8120364 (published as GB No. 2081258A) and in its following corresponding applications: Australian patent application No. 81/72999, Canadian patent application No. 380907, European patent application No. 81303000.4, Japanese patent application No. 81/502230, New Zealand patent application No. 197558, South African patent application No. 81/4307 and U.S. Pat. application No. 349,084.

The compounds described in these earlier applications contain a divalent cyclic group carrying two specific types of side chain which are required to confer the desired activity at thromboxane receptor sites. We have now found, however, that compounds containing a side chain of a markedly different type are also of interest for their activity at thromboxane receptor sites. Thus, the earlier compounds all contain a first side chain which is a 6-carboxyhex-2Z-enyl group or a modification thereof and a second side chain which may be of a wide variety of types, each of which types however contains a grouping of the form >C=N— at the point of attachment of this second side chain to the divalent cyclic group. The compounds of the present application are quite distinct in that their second side chain does not contain such a grouping.

SUMMARY OF THE INVENTION

Accordingly the present invention comprises a compound of formula (I)

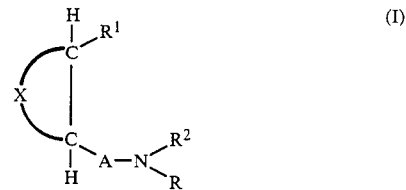

wherein

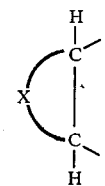

represents one of the divalent cyclic groups shown below:

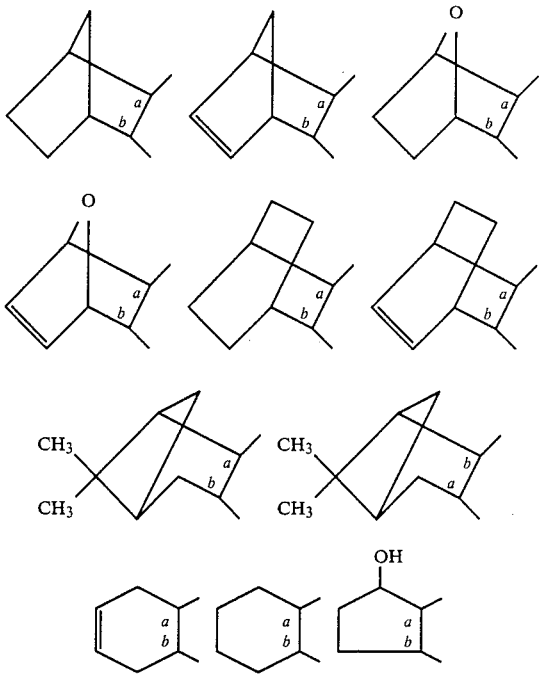

the letters a and b indicating in each case the points of attachment of the substituents $R^1$ and A—$NR^2R$, respectively; $R^1$ is a 6-carboxyhex-2-enyl group or a modification thereof in which the group is altered by one, or an appropriate combination of two or more, of the following: (a) alteration of the position of the double bond, (b) reduction of the double bond, (c) replacement of a methylene group at any of positions 1 to 5 by an oxygen or sulphur atom, (d) alteration of the chain length through a decrease or an increase of one or two methylene groups, and (e) formation of an amide, ester or salt derivative of the carboxy group; A is an aliphatic hydrocarbon group with a chain length between the points of attachment to the divalent cyclic group and to the group $NR^2R$ of 1 to 5 carbon atoms or such a group substituted by an aromatic group; $R^2$ is hydrogen, an aliphatic hydrocarbon group, an aromatic group or an aliphatic hydrocarbon group substituted by an aromatic group or groups; and R is a group —CO.NR$^3$R$^4$, —CS.NR$^3$R$^4$, —CNH.NR$^3$R$^4$, —CO.R$^4$ or —CS.R$^4$ in which R$^3$ is hydrogen, an aliphatic hydrocarbon group, an aromatic group or an aliphatic hydrocarbon group substituted by an aromatic group or groups but with the proviso that both R$^2$ and R$^3$ may not be other than hydrogen, and R$^4$ is an aliphatic hydrocarbon group, an aromatic group or an aliphatic hydrocarbon group substituted directly by an aromatic group or groups and/or through an oxygen or sulphur atom either by an aromatic group or by an aliphatic hydrocarbon group substituted directly by an aromatic group or groups.

DETAILED DESCRIPTION OF THE PREFERRED EMBODIMENTS

The various bridged ring systems indicated above may alternatively be represented in planar form, i.e. in the same order as:

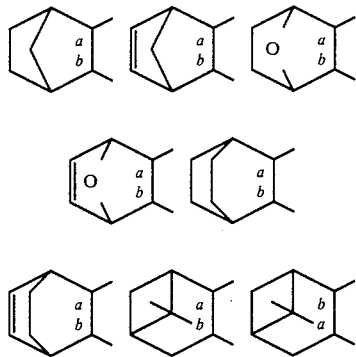

(the two free valencies in the centre of the last two formulae indicating methyl groups), but the more usual convention has generally been followed throughout the specification of representing these systems in non-planar form. It will be appreciated, however, that the compounds (I) may exist in various stereoisomeric forms, which are included within the scope of the invention, and in particular that each geometric isomer of a bridged ring compound (I) will exist in two enantiomorphic forms. These two forms will have the structure illustrated hereinbefore and the mirror image of that structure. Taking the vicinally disubstituted bicyclo [2,2,1] heptane ring system as an example, such pairs of enantiomorphs may be shown as follows (the rings being numbered according to the system used herein).

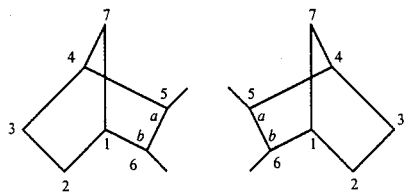

For the sake of added clarity it might be mentioned that alternative, equivalent, modes of showing these non-planar structures may be used. Thus the right hand of the two formulae shown directly above is equivalent to:

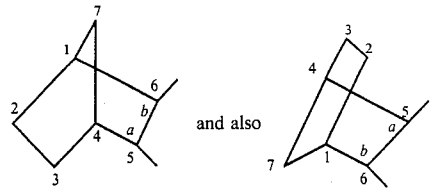

It will be seen that the modifications of the 6-carboxyhex-2-enyl group which may be made in compounds according to the present invention are of two types. Thus, the modifications either involve the hex-2-enyl group or the 6-carboxy group. Among the modifications of the first form, which are listed under (a) to (d) above, certain preferences may be indicated. Thus, if the position of the double bond is altered, it is conveniently to the 3,4-position of the 6-carboxyhex-2-enyl group, although compounds in which the double bond is reduced are also of some interest. Although a methylene group at any of positions 1 to 5 may be replaced by a sulphur or especially an oxygen atom, preference is for replacement of a group at the 2 or 3 position (in conjunction with reduction of the double bond) or even the 1 position. A chain of six atoms substituted by a carboxy group is preferred but where the chain length is altered an increase in chain length is of generally greater interest than a decrease and a change of one methylene group only is preferred, particularly when a decrease is involved.

As regards the second type of modification of form (e) as indicated above the carboxy group derivatives may be (a) esters, especially alkyl esters, for example those containing a $C_1$-$C_{10}$ alkyl group but particularly methyl esters; (b) amides, which may contain a group —CONH$_2$ or such a group in which the nitrogen atom is substituted, especially by one or two groups selected from substituted or unsubstituted phenyl groups, for example as described hereinafter, alkyl groups, for example $C_1$-$C_{10}$ alkyl groups, and from more complex groups such as —SO$_2$CH$_3$ or an analogue thereof containing a $C_2$-$C_{10}$ alkyl group, for example to provide a group of the form —CONHSO$_2$CH$_3$; and (c) salts with various physiologically acceptable cations. Salt derivatives are of especial interest, specific examples of salts being those formed with an alkali metal such as sodium or with quaternary ammonium ions or amines such as tris (the symbol tris represents the compound 2-amino-2-hydroxymethylpropane 1,3-diol). It will be appreciated that many of such compounds containing a modification of form (e) are in fact bioprecursors for the corresponding compound containing a carboxy group to which they are converted in vivo.

Examples of specific groups R$^1$ are —CH$_2$—CH═CH—(CH$_2$)$_3$CO$_2$H, —(CH$_2$)$_6$CO$_2$H and —(CH$_2$)$_2$O(CH$_2$)$_3$CO$_2$H, and derivatives formed at the carboxy groups thereof.

The divalent aliphatic hydrocarbon group A may be fully saturated or contain unsaturation. Groups with a chain length of 1 to 5, particularly 1, 3 or especially 2 carbon atoms are preferred and fully saturated groups are also of particular interest. Both unbranched and branched groups are of interest, and although branching may be present at other carbon atoms of the group A, groups which show branching at the carbon atom bonded to the divalent cyclic group (C$_1$) are of some particular interest. Aliphatic hydrocarbon groups which constitute a branch from the chain of carbon atoms linking the divalent cyclic group and the group $NR^2R$ may be of the type described hereinafter in relation to the group $R^4$ but acyclic groups and especially alkyl groups are preferred. The size of such branched groups can however sometimes influence the ease with which the compounds (I) may be prepared and they are therefore preferably of 1 to 3 carbon atoms, for example being an alkyl group such as ethyl and especially methyl. Most usually, therefore, the overall size of the aliphatic hydrocarbon group A is no more than 10 carbon atoms and it may often be in the range from 1 to 5 carbon atoms.

As indicated, A may also be an aliphatic hydrocarbon group substituted by an aromatic group. Such groups A are of less interest but when used are preferably derived from aliphatic hydrocarbon groups A of the type specifically described above, for example groups with a chain length of 1 to 3 carbon atoms. The aromatic group may be substituted on the chain of carbon atoms linking the divalent cyclic group and the group $NR^2R$ or on an aliphatic hydrocarbon group which constitutes a branch from this chain. Substitution either on the carbon atom of the chain which is bonded to the divalent cyclic group ($C_1$) or, especially, on a group branched from the chain at this point is of particular interest. It may be advantageous, however, for the aromatic group to be separated from the $C_1$ carbon atom by one or especially two carbon atoms so that, in the preferred case where the aromatic group is substituted on a branch at the $C_1$ carbon atom, the branched group may be a phenylmethylene or 1-phenylethylene group or especially a 2-phenylethylene group. The aromatic group may be as described for $R^4$ hereinafter but unsubstituted and substituted pyridine and phenyl groups are of particular interest, for example an unsubstituted phenyl group.

Specific groups A of particular interest are those unbranched groups consisting of a number of methylene groups, particularly of 1 or 3 and especially of 2 such groups, and also groups of a similar chain length which are branched at $C_2$ or particularly at $C_1$. Examples of such alkylene groups A are $-CH_2-$, $-CH_2CH_2-$, $-CH(CH_3)CH_2-$, $-CH_2CH(CH_3)-$, and $-CH_2CH_2CH_2-$. Also of some interest are unsaturated groups. When A is an unsaturated group, however, it is preferred that the carbon atom bonded to the group $NR^2R$ is saturated in view of the relative instability of the grouping $-CH=CH-N<$, unsaturated substituent groups $-A-NR^2R$ of the form $-CH=CH-CH_2-NR^2R$ being of particular interest.

Compounds in which $R^2$ is hydrogen are of particular interest but, in the case of compounds where this is not the case, the group $R^2$ is more usually one of the aromatic and unsubstituted or directly substituted aliphatic groups of the type described hereinafter in relation to the group $R^4$. Aliphatic hydrocarbon groups substituted by one aromatic group, unsubstituted aromatic hydrocarbon groups such as phenyl and particularly unsubstituted aliphatic hydrocarbon groups are of especial interest. In general, compounds in which $R^2$ is an acyclic aliphatic group, especially one of the smaller alkyl groups of 1 to 3 carbon atoms, for example methyl and ethyl, or particularly hydrogen are preferred.

Among the various types of group R, those of the type $-CO.NR^3R^4$, and $-CS.NR^3R^4$ are of some especial interest although other groups R and particularly $-CNH.NR^3 R^4$ are also of interest. As regards the group $R^3$, preferences are generally as expressed above for the group $R^2$ although groups other than hydrogen have an added interest in this case through prevention of the "keto-enol" type of isomerism present between a group $-NHR^4$ and an adjacent carbonyl group, etc. It should be noted however that $R^3$ may only be other than hydrogen when $R^2$ is hydrogen and vice-versa.

As indicated, the group R can contain groups $R^4$ of various forms. Aliphatic hydrocarbon groups constituting $R^4$ may conveniently be of one to five, six, seven, eight, nine, ten or even more carbon atoms being, for example, an alkyl group which may be branched or unbranched such as methyl, ethyl, propyl, butyl, amyl, etc. and also cycloalkyl groups such as cyclopentyl, cyclohexyl, etc., as well as combinations of alkyl and cycloalkyl groups such as cyclohexylmethyl, etc.

Aromatic groups constituting $R^4$ are of greater interest than the unsubstituted aliphatic hydrocarbon groups and may be hydrocarbon or heterocyclic groups which may be unsubstituted or substituted. Moreover, the term 'aromatic group' as used herein extends to groups derived from ring systems having aromatic properties but in which the $\pi$-electron system is not fully delocalised over the entire ring system, such groups including those derived from fluorene, 1,2,4,5-dibenzocyclohexane, 1,2,4,5-dibenzocycloheptane, dihydrobenzoxazole, dihydrobenzthiazole and N-methyldihydrobenzthiazole. The heterocyclic groups, which conveniently contain one, two or more, similar or different nitrogen, oxygen or sulphur atoms, are more generally linked through a carbon atom so that, in the case of a pyridyl group, pyrid-2-yl, pyrid-3-yl, and pyrid-4-yl, are or particular interest. Moreover, in the case of those groups containing one or more benzene rings together with one or more non-benzenoid rings, such as those derived from fluorene and its cyclohexyl and cycloheptyl analogues, and from benzthiazole, dihydrobenzthiazole. N-methyldihydrobenzthiazole and their benzoxazole analogues, linkage of the group is more usually effected through a nonbenzenoid ring.

Among the aromatic groups constituting $R^4$, aromatic hydrocarbon groups, for example napthyl and particularly phenyl, are however, generally of rather greater interest than heterocyclic groups. Both the aromatic hydrocarbon and the heterocyclic groups may be substituted by one or more of various types of substituent, particularly by alkoxy groups, for example those containing alkyl groups of 1,2,3 or more carbon atoms as described above, and especially methoxy, and by substituents being or containing a halogen residue, for example chloro and especially fluoro and also halogen substituted alkyl groups such as $CF_3$. Examples of other substituents are sulphamoyl groups which may optionally be N-substituted, amino groups which may be free or substituted, for example dimethylamino, and hydroxyl, nitro, and alkyl groups which may, for example, be of 1 to 3 carbon atoms or otherwise as described above, etc. Substitution may be present at one of the ortho, meta and para positions of a phenyl ring or at a combination of two or more such positions (including two similar positions), for example at the 2 and 4 or 3 and 4 positions. Substitution and the position of substitution, particularly by alkoxy groups such as methoxy and groups being or containing a halogen residue, may have a definite effect upon the level of activity of a compound, for example, p-methoxy substituents being of particular interest.

The third possible type of group $R^4$ is an aliphatic hydrocarbon group substituted directly by an aromatic group or groups and/or through a sulphur or particularly an oxygen atom either by an aromatic group or by an aliphatic hydrocarbon group substituted directly by an aromatic group or groups. Both the aliphatic hydrocarbon group attached to the nitrogen atom of the group

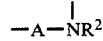

and any additional aliphatic hydrocarbon group attached thereto through an oxygen or sulphur atom may be of a similar size to those described above but preferably comprise an acyclic group, conveniently of 3 carbon atoms, particularly of 2 carbon atoms and especially of 1 carbon atom, although this acyclic group may carry a cyclo-alkyl group as well as an aromatic group. Preferred acyclic groups take the form of unbranched alkylene groups such as methylene, ethylene or propylene, or corresponding trivalent groups of similar size. Similar aromatic hydrocarbon and heterocyclic residues are generally of interest for attachment to the aliphatic groups as have already been described above, the aromatic hydrocarbon groups again generally being of rather more interest than the heterocyclic groups. Heterocyclic groups, where used, are of most interest in this context when linked to the aliphatic hydrocarbon group through a hetero atom such as in pyrid-1-yl. Substitution of an aliphatic hydrocarbon group, particularly terminally, by two or even three aromatic groups, for example phenyl, is of some interest, whilst also of interest are acyclic groups carrying terminally both an aromatic group, for example phenyl, and a cyclo-alkyl group, for example cyclohexyl.

Compounds in which the group $R^4$ of the group R is an aliphatic hydrocarbon group substituted directly by an aromatic group, for example in the manner just described, are of considerable interest. However, also of much interest are compounds in which the group, or one of the groups, by which the aliphatic hydrocarbon group is substituted is an araliphatic group or especially an aromatic group which is attached thereto through a sulphur or particularly an oxygen atom. In such a case, however, the sulphur or oxygen atom is preferably not attached to the carbon atom of the aliphatic hydrocarbon group which is attached to the remaining part of the group R.

Examples of specific groups $R^4$ are:

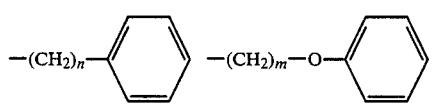

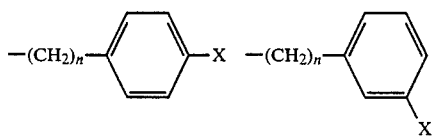

-continued

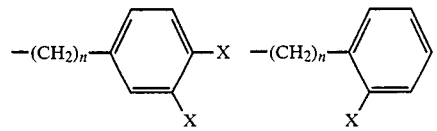

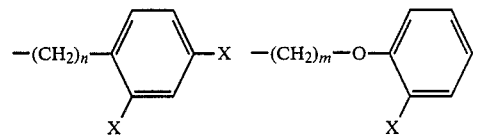

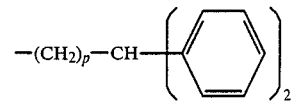

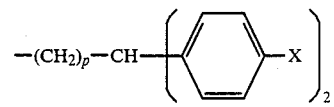

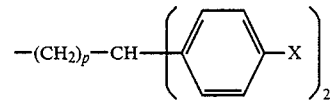

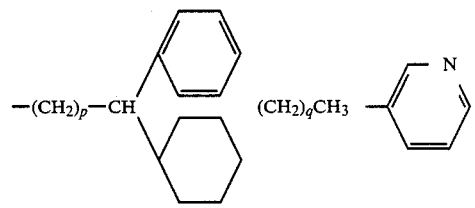

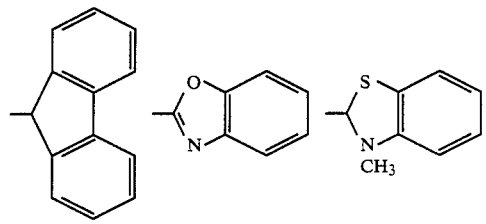

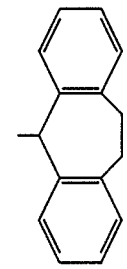

wherein n=0, 1, 2 or 3, m=1, 2 or 3 (but particularly 2 or 3 as indicated above), p=0, 1, or 2, q=1, 2, 3, 4 or 5 and X=OCH$_3$, Cl, F, CF$_3$ or CH$_3$.

As indicated above, compounds according to the present invention may contain, in the order shown previously, one of the following types of right systems: bicyclo [2,2,1] heptane, bicyclo [2,2,1] hept-2Z-ene, 7-oxa-bicyclo [2,2,1] heptane, 7-oxa-bicyclo [2,2,1] hept-2Z-ene, bicyclo [2,2,2] octane, bicyclo [2,2,2] oct- 2Z-ene, 6,6-dimethyl-bicyclo [3,1,1] heptane, cyclohexene, cyclohexane and hydroxycyclopentane. The 6,6-dimethyl-bicyclo [3,1,1] heptane ring system, unlike the others, may be substituted in either of two ways, corresponding to reversal of the substituents shown at the a and b positions. It will be appreciated that the bridged ring systems present in compounds according to the present invention show a range of degrees of asymmetry. Thus, the 6,6-dimethyl-bicyclo [3,1,1] heptane ring system is sufficiently asymmetric for reversal of the substituents at the a and b positions to result in a different structural isomer, and thus a different compound (I), both types of compound (I) containing the 6,6-dimethyl-bicyclo [3,1,1] heptane ring system being covered by the present invention although that having the group $R^1$ at position 3 is perhaps of most interest. In the case of the bicyclo [2,2,1] heptane and bicyclo [2,2,1] hept-2Z-ene ring systems and their 7-oxa analogues, however, reversal of these substituents would merely provide a structure which represents an alternative stereoisomer, the invention, as has previously been indicated, extending to the compounds (I) in their various stereoisomeric forms. The situation with the bicyclo [2,2,2] oct-2Z-ene ring system is similar to that pertaining in the case of its 7-membered analogue but the bicyclo [2,2,2] octane ring system has a sufficient degree of symmetry for such reversal of the a and b substitutents to give the same compound (I) of identical stereochemistry. Among the divalent cyclic groups present in the compounds of this invention, the bridged ring systems are of particular interest and of these the bicyclo [2,2,1] hept-2Z-ene and especially the bicyclo [2,2,1] heptane systems may be mentioned particularly. Among those bridged ring systems which may be saturated or unsaturated, the former are usually preferred, particularly in the case of the compounds containing an oxygen bridging group, as unsaturation generally confers lower stability whilst the level of biological activity is generally substantially similar.

It will be appreciated that the structures of the compounds described above provide various opportunities for the occurrence of stereoisomerism. The substituent groups $R^1$ and $A—NR^2R$ may be in the cis or trans relationship to each other, compounds of the latter configuration more generally being preferred. Moreover, when the ring system is one which is bridged or contains a hydroxy substituent then, in most cases, different isomers will exist which vary according to the way in which the substitutent groups $R^1$ and $A—NR^2R$ are disposed in relation to the bridging groups or the substituent. Isomers of particular interest are shown below in one of the two enantiomorphic forms which can exist in each case, the other enantiomorph having a structure which is the mirror image of that shown. The unsaturated ring system is illustrated when the ring system may be saturated or unsaturated and the symbol X represents —CH$_2$— (position 7), —O— (position 7) or —CH$_2$CH$_2$— (positions 7 and 8). As indicated above, the bicyclo [2,2,2] octane system possesses a greater degree of symmetry than the other bridged ring systems, as the two bridging groups attached together at the bridge positions (1 and 4) are identical, both being —CH$_2$CH$_2$—. In this case therefore, although the trans isomer is preferred and can exist in two enantiomorphic forms, the endo, exo type isomerism which can occur with the other bridged ring systems cannot arise.

It will be seen that in the structures shown below the numbering applied herein to the various positions of the ring systems has been indicated. It should be noted that the system of numbering adopted for the bridged ring systems which can exist in both saturated and unsaturated form is chosen so that the double bond in the unsaturated ring system receives the lowest number possible (2), the substituents $R^1$ and $A—NR^2R$ then being at the 5 and 6 positions respectively. For conformity, a similar system of numbering is followed for the analogous saturated ring systems, the substituents again being described as at the 5 and 6 positions, rather than the 2 and 3 positions as in the 6,6-dimethyl [3,1,1] heptane system.

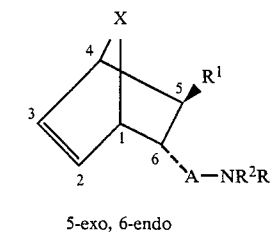

5-exo, 6-endo

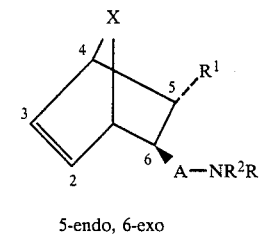

5-endo, 6-exo

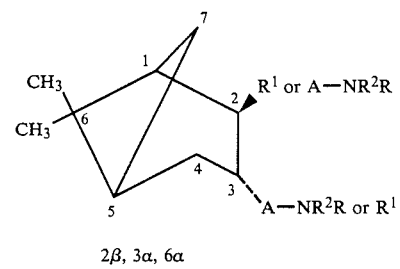

2β, 3α, 6α

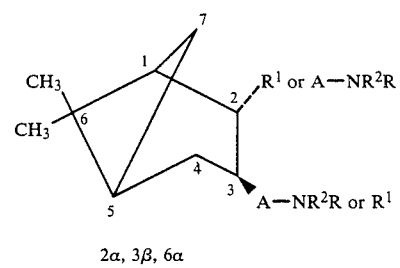

2α, 3β, 6α

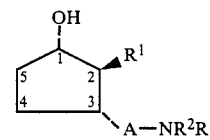

1α, 2β, 3α

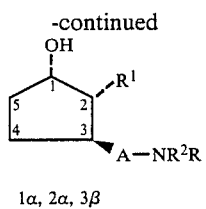

1α, 2α, 3β

Among the isomers illustrated above, of the two forms shown in each case, one is usually preferred to a somewhat greater extent than the other. In the case of the 5-exo, 6-endo and 5-endo, 6-exo isomers the latter is most usually preferred but in the case where X is —O— the 5-exo, 6-endo isomer is also of considerable interest. In the case of 2β, 3α, 6α, and 2α, 3β, 6α isomers the latter is of most interest. The convention applied herein for naming the compounds (I) containing a 6,6-dimethyl-bicyclo [3,1,1] heptane ring system is the use of α and β to indicate the directions in which the substituents at the 2- and 3-positions are directed. In the designations used above the position of the bridging carbon atom at position 6 has for simplicity also been indicated by an α or a β (the position of the gem dimethyl groups at the 6-position is dictated by that of the carbon atom to which they are attached). In the case of the 1α, 2β, 3α and 1α, 2α, 3β isomers the latter is again of most interest.

Where the substituent $R^1$ is a 6-carboxyhex-2-enyl group or a group modified therefrom but still containing the double bond, then the configuration about this bond is preferably cis (Z) rather than trans (E). In addition to the foregoing isomerism, as indicated previously the compounds of the present invention will in most cases additionally be resolvable into enantiomorphic forms and one among these may be preferred by virtue of biological activity or physical properties. Single enantiomers may be obtained either by the use of an optically active starting material or by resolution of a pair of enantiomorphs.

Specific compounds according to the present invention include the compounds of formula:

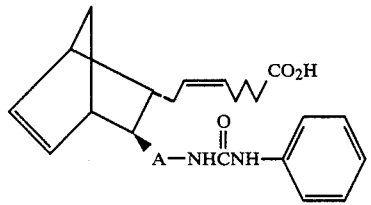

A being —CH$_2$—, —CH$_2$CH$_2$—, —CH(CH$_3$)CH$_2$—, —CH$_2$CH(CH$_3$)— or —CH$_2$CH$_2$CH$_2$—, as well as the analogues thereof in which the bicyclo [2,2,1] hept-2Z-ene ring is replaced by a bicyclo [2,2,1] heptane ring and/or the 6-carboxy-hex-2Z-enyl group is replaced by a 6-carboxyhexyl group and/or the other substituent grouping is replaced by a grouping

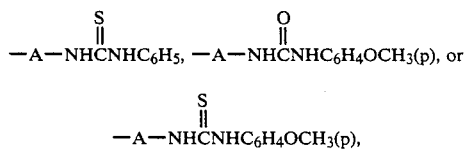

in which A is as just defined, as well as ester, amide and salt derivatives thereof.

The various compounds of formula (I) according to the present invention may conveniently be prepared from an intermediate of formula (II).

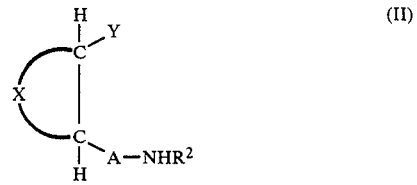

in which Y is either $R^1$ as defined hereinbefore for compound (I) or a precursor for $R^1$ and the other symbols are as defined hereinbefore for compound (I) but with the letters a and b relating instead to the substituents Y and A—NHR$^2$, respectively. Such compounds (II) are included by the present invention in view of their value as intermediates. When the compound (I) contains a group R of the form —CO.NHR$^4$ or —CS.NHR$^4$ the appropriate compound (II) is conveniently reacted with an isocyanate R'NCO or isothiocyanate R'NCS in which R' is either R$^4$ or a group convertible thereto. When the compound (I) contains a group R of the form —COR$^4$ then the compound (II) is conveniently reacted with an acylating agent R'COW in which R' is either R$^4$ or a group convertible thereto and W is a suitable leaving group such as a halogen atom, for example chlorine, or an alkoxy group, for example methoxy. Alternatively, an acid anhydride (R'CO)$_2$O may be used in which R' is either R$^4$ or a group convertible thereto. When the compound (I) contains a group R of the form —CNH.NHR$^4$ the compound may conveniently be prepared through utilising one of the routes to guanidino groups described in UK Patent Specification No. 1492678. Thus, for example, the corresponding compound containing a group —CS.NHR$^4$ may be treated with ammonia in the presence of a heavy metal oxide catalyst to convert this group to a group —CNH.NHR$^4$ or, alternatively, the compound (II) may be reacted with a cyanamide R'NHCN in which R' is either R$^4$ or a group convertible thereto. When the compound (I) contains a group R of the form —CSR$^4$, then the group —A—NH$_2$ (R$^2$ being hydrogen) of the compound (II) may conveniently be converted to a group —A—N=C=S in which the amino group is replaced by an isothiocyanato group, for example by the use of carbon disulphide in the presence of dicyclohexylcarbodiimide at about −10° C., which group may then be reacted with a Grignard reagent R'MgX in which R' is either R$^4$ or a group convertible thereto and X is a halogen residue, for example bromo, to give the group —A—NH—CSR$^4$.

Most usually the group R' in the reactant is R$^4$ but where this is not the case or where Y is not $R^1$ then the synthesis of the compound (I) is concluded by the conversion of R' and/or Y to R$^4$ and/or $R^1$, respectively. Thus, for example, when $R^1$ contains a free carboxy group then the group Y in the compound of formula (II) may similarly contain a free carboxy group or a carboxy group in protected form, for example as an ester and particularly as the methyl ester which may conveniently be formed with diazomethane. Following reaction with the reactant R'NCO, R'NCS, R'COW, (R'CO)$_2$O, R'NHCN, R'MgX, etc., such a protecting group may then be removed, for example by de-esterification using KOH/CH₃OH/H₂O. Such protection may lead to a greater overall yield of the compound (I) from the compound (II).

When the compound (II) contains a group —CO.NR³R⁴, —CS.NR³R⁴, or —CNH.NHR³R⁴, in which R³ is other than hydrogen, variations of the above described procedures are employed. Thus, for the introduction of such a group —CO.NR³R⁴, the group —A—NH₂ (R² being hydrogen) of the appropriate compound (II) may conveniently be converted to a group —A—N=C=O in which the amino group is replaced by an isocyanato group, for example by the use of phosgene, which group may then be reacted with a secondary amine HNR'R" in which R" is either R³ or a group convertible thereto and R' is either R⁴ or a group convertible thereto. For the introduction of a group —CS.NR³R⁴ in which R³ is other than hydrogen, a compound as described above may be used in which the group —A—NH₂ (R² being hydrogen) of the compound (II) has been converted to a group —A—N=C=S, the isothiocyanato group then being reacted with a secondary amine HNR'R". For the introduction of a group —CNH.NR³R⁴ in which R³ is other than hydrogen, the corresponding compound containing a group —CS.NH'R", in which R' and R" are as defined above, may be treated with ammonia in the presence of a heavy metal catalyst. Other alternatives for the introduction of such a group include the conversion of the group —A—NH₂ (R² being hydrogen) of the compound (II) to a group —A—NH—C≡N in which the amino group is replaced by a cyanamido group, for example via a group —A—N=C=S as discussed above, which may be reacted with ammonia to form a group —A—NH—CS—NH₂ containing a thioureido group which is in turn treated with yellow mercuric oxide to give the group —A—NH—C≡N. Reaction of this cyanamido group with a secondary amine HNR'R" then ultimately yields the desired group —CNH.NR³R⁴. Modifications of the groups R', R" and Y, where necessary, may be effected at the end of all synthesis although R" and R' are most usually identical to R³ and R⁴ respectively.

The compounds described above in which the amino group of the group —A—NH₂ of compounds (II) is replaced by an isocyanato, isothiocyanato or cyanamido group are included by the present invention in view of their value as intermediates.

The compounds of formula (II) may conveniently be prepared from an intermediate of formula (III):

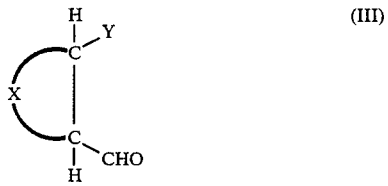

(III)

in which Y is as defined above for compound (I) or is R' a precursor for R¹. The preparation of compounds (III) is fully described in application No. GB 2081258A and its corresponding applications (U.S. Pat. Application Ser. No. 349,084, now U.S. 4,596,823.) Modified 6-carboxyhex-2-enyl groups which involve alteration of the hex-2-enyl group are usually introduced into the compound (III) through a variation in the procedure which yields the corresponding compound containing a 6-carboxyhex-2-enyl group. Certain of such variations are described in that application and others include addition of a modified 6-carboxyhex-2-enyl group initially in the form of a substituent grouping terminating in a hydroxymethyl group which is then subsequently oxidized to a carboxy group. Modified 6-carboxyhex-2-enyl groups which involve alteration of the carboxy group are more amenable to being made, if desired, at a later stage in the synthesis of the compound (I).

The procedures for the conversion of a compound (III) to a compound (II) conveniently involve an initial modification of the group —CHO, where appropriate, to form a group —B=O wherein B is a trivalent aliphatic hydrocarbon group corresponding to the divalent group A but with the replacement by a free valency of a hydrogen atom attached to that carbon atom of the group A which is nitrogen-bonded, this carbon atom together with the oxo group forming a carbonyl group at the end of the group —B=O (when —A— is —CH₂—, —B=O will be —CHO and no modification is required). The group —B=O may then be converted to the desired group —A—NH₂ by reductive amination. Such reductive amination may conveniently involve reaction of the carbonyl group with a suitable ammonium salt such as ammonium acetate to produce an iminium group —B=N⁺H₂ which may then be reduced using a suitable reducing agent such as borohydride, particularly sodium cyanoborohydride in view of the acidic conditions, to form the group —A—NH₂. When R² is other than hydrogen, various procedures described in the art for the preparation of secondary amines may be employed, for example alkylation of the primary amine described above or reaction of the group —B=O with an amine R²NH₂ to form a group —A—NHR².

Appropriate modifications of the group —CHO of compound (III) to produce a group —B=O may readily be achieved by the use of a variety of procedures described in the art for such a purpose. Where appropriate, the group —CHO may initially be modified to the form —CR'''O in which R''' is an aliphatic hydrocarbon group, an aromatic group or an aliphatic hydrocarbon group substituted by an aromatic group. Such a group —CR'''O then provides a suitable precursor for a group A having such an unsubstituted or substituted aliphatic hydrocarbon group or aromatic group on the carbon atom adjacent to the divalent cyclic group of the chain joining this group to the group NR²R. Procedures for effecting such a modification are fully described in application GB 2081258A, the procedure for introducing an aromatic group being similar to that for an unsubstituted or substituted aliphatic group. Where appropriate, the group —CHO or —CR'''O may then be chain extended by various procedures described in the art for such a purpose to provide the desired group —B=O. Thus, for example, chain extension by one carbon atom may be effected by reaction of the group —CHO or —CR'''O with nitromethane, conveniently in a solvent such as isopropanol with a catalytic amount of potassium fluoride over about 6 hours at room temperature. The resulting group —CHOH—CH₂NO₂ or —CR'''OH—CH₂NO₂ may then be converted to a group —CH₂—CH₂NO₂ or —CHR'''—CH₂NO₂ through heating with acetic anhydride followed by sodium borohydride reduction (—CHOH—CH₂NO₂→—CH=CHNO₂→—CH₂—CH₂NO₂) or using acetic anhydride with N,N-dimethylaminopyridine as a catalyst followed by sodium borohydride reduction (—CHOH—CH₂NO₂→—CHOAc—CH₂NO₂→—CH₂—CH₂NO₂). A Nef reaction may then be employed to produce a group —CH₂—CHO or —CR'''—CHO. Thus for example, sodium methoxide followed by sulphuric acid in methanol will convert a group —CH₂—CH₂—NO₂ to the acetal —CH₂—CH(OCH₃)₂ which may be hydrolysed with hydrochloric acid in chloroform to give a group —CH₂—CHO.

For the production of compounds containing larger groups A, one convenient procedure involves the use of a crossed aldol condensation, following at a suitable point when a saturated group A is required by a reduction step. Thus a group —CHO or —CR'''O may be reacted with acetaldehyde to effect condensation followed by dehydration with the formation of a group —CH=CH—CHO or —CR'''=CH—CHO. Variations of this approach will yield groups A with a chain or 3 or 4 carbon atoms, for example by the reaction of a group —CHO or —CR'''O with crotonaldehyde or of a group —CH₂—CH₂—CHO or —CHR'''—CH₂—CHO with acetaldehyde. Alternative routes include the use of dihydrotetramethyloxazine, which will add to a group —CHO to produce, after reduction with sodium borohydride and acid hydrolysis, a group —CH=CH—CHO, and similarly for addition to a group —CR'''O

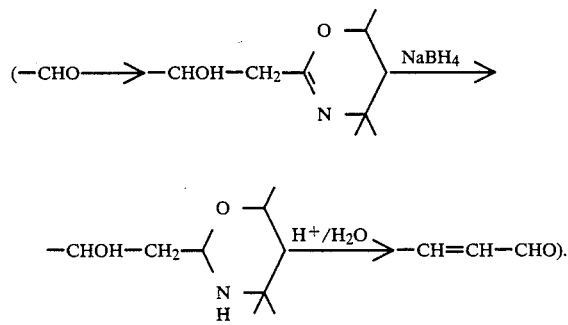

A group —CH₂—CH₂—CHO or —CHR'''—CH₂—CHO may be produced directly, rather than through reduction of the thus produced group —CH=CH—CHO or —CR'''=CH—CHO, by effecting dehydration before barohydride reduction

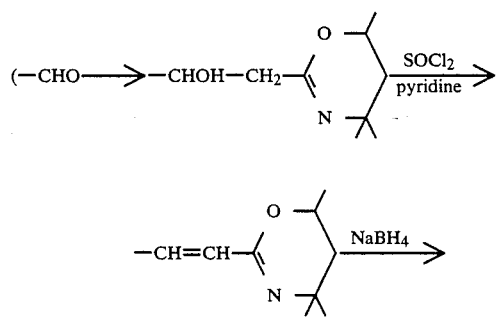

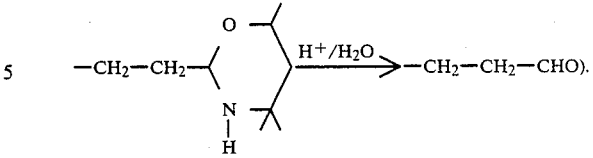

Such a procedure may be of value in avoiding concomitant reduction of a double bond in the divalent cyclic group.

Variations of these procedures may be used to produce alternative branched and/or substituted groups A, the use of nitroethane in place of nitromethane, for example, providing a group —CH₂—CH(CH₃)NH₂ and a similar procedure to that used for the conversion of a group —CHO to —CR'''O being applicable to modification of a terminal CHO group to produce a group —B=O in which the terminal carbonyl group is of the form —C(aliphatic hydrocarbon group)=O or —C(aromatic group)=O.

The various compounds described herein containing a group —B=O (other than —CHO or —CR'''O) are included in this invention by virtue of their value as intermediates.

It will be appreciated that the methods described above are not the only ones which may be used for the preparation of compounds according to the present invention and that various alternative procedures may be used as will be apparent to those skilled in the art.

Pharmaceutical compositions containing compounds according to the present invention are of interest in various contexts for their inhibition of thromboxane activity, which is believed to be caused by a thromboxane antagonism, uses including the treatment of thrombotic disorders and also the treatment of anaphylactic disease states, for example as bronchodilators for the treatment of asthma, in hypoxia, etc. they additionally have potential as antiinflammatory agents. It will be appreciated that the spectrum of activity shown by any particular compound will vary and that certain compounds may be of particular interest in one of these applications whilst other compounds are of particular interest in another of them. Moreover, although preferred compounds such as those of Examples 2 and 8 show a pure antagonist activity in the rabbit aorta system, some other compounds may show a partial agonist activity in this test although they are antagonists in the human platelet system. Any compounds showing such a partial enhancing action on the thromboxane activity are also of some interest in respect of this activity although to a much lesser extent than with inhibitory activity. Thus, certain compounds according to the present invention may be of interest for laboratory or even for pharmaceutical purposes, for example in the control of bleeding by topical administration which avoids any systemic take-up, by virtue of the thromboxane enhancing facet of their activity which is shown under certain conditions.

Modifications of the 6-carboxyhex-2-enyl group may be of value in imparting a particular property to a compound which is of value in its formulation. Thus, for example, esters and other carboxy group derivatives of this group or of modifications thereof in which the hex-2-enyl group is altered can have advantages in relation to slow release depot preparations through their conversion in vivo to the compound containing a free carboxy group, although the low water solubility of the esters must be taken account of. Alternatively, the use of a compound in which the carboxy group is in salt form, for example the sodium salt, can be of value due to the enhancement of water solubility which generally results.

The compounds may be formulated for use as pharmaceuticals for both animal and particularly human administration by a variety of methods, but usually together with a physiologically acceptable diluent or carrier. The compounds may, for instance, be applied as an aqueous or oily solution or as an emulsion for parenteral administration, the composition therefore preferably being sterile and pyrogen-free. The compounds may also be compounded for oral administration in the presence of conventional solid carrier materials such as starch, lactose, dextrin and magnesium stearate. Alternative formulations are as aerosols, suppositories, cachets, and, for localised treatment, as suitable creams or drops. Without commitment to a rigid definition of dosage, which is difficult in view of the different levels of activity, methods of formulation, and methods of administration, some general guidance may be given. In the case of systemic administration to produce a thromboxane antagonism the normal daily dosage which is proposed lies in the range from about 0.1 mg to about 10 mg per kilogram (the average weight of a human being about 70 kg) and particularly from about 1 mg to about 5 mg per kilogram. It will be appreciated, however, that dosages outside this range may be considered, for example in the case of topical application to produce a localised thromboxane agonism, and that the daily dosage may be divided into two or more portions.

The invention is illustrated by the following Examples.

In the Examples the stereochemistry which the compounds are believed to possess has been indicated, the various bicyclo [2,2,1] heptanes and hept-2Z-enes being obtained in the form of a racemic mixture. However, some contamination of a minor nature by other isomers may often be present, i.e. by the other of the pairs of preferred trans isomers or particularly by the corresponding cis isomer. It will be appreciated that the proportion of such contaminants does not necessarily depend upon the stereochemical nature of the intermediates in earlier stages of the synthesis. Thus certain compounds are capable of epimerisation under particular conditions and the compounds (III) in particular can undergo an epimerisation involving the formyl group under some circumstances, for example when these products are generated by the action of acid on an acetal.

It will be appreciated that 5-endo-(6'-methoxycarbonylhex-2'Z-enyl)-6-exo-formyl-bicyclo [2,2,1] hept-2Z-ene may be replaced in the procedures of Examples 4, 5 and 6 by the corresponding heptane to provide, together with the compound of Example 1, a group of intermediates for the preparation of all of the heptane analogues of the hept-2Z-ene compounds of Examples 7 and 8. Moreover, as mentioned previously, additional intermediate compounds (III) containing various other ring systems are described in application GB No. 2081258A and its corresponding applications (U.S. Pat. Application Ser. No. 349,084, now U.S. Pat. No. 4,596,823) and such compounds may be used as alternatives to 5-endo-(6'-methoxycarbonylhex-2'Z-enyl)-6-exo-formyl-bicyclo [2,2,1] hept-2Z-ene in the procedures of Examples 3, 4, 5 and 6 to provide intermediates for the preparation of analogues of the compounds of Examples 7 and 8 containing different ring systems.

Unless otherwise indicated, the mass spectroscopy data given in the Examples is obtained by direct inlet in the case of compounds of formula (I) and by gas chromatography mass spectroscopy in the case of intermediates used in the preparation of these compounds.

EXAMPLES

Example 1

5-endo-(6'-Methoxycarbonylhex-2'Z-enyl)-6-exo-aminomethylbicyclo [2,2,1] heptane (1) Maleinaldehydic acid pseudo-ethyl ester 30 g of redistilled furan-2-aldehyde is mixed with 600 ml dry ethanol and 300 mg of methylene blue is added. Dry air is blown gently through the solution and the material is irradiated with a 300 W tungsten lamp for about two days until t.l.c. in a silica gel/ether system shows essentially no remaining starting material. The solution is then stirred with vanadium pentoxide for four hours, filtered, and the solvent removed under reduced pressure. The residual oil is distilled under high vacuum to give the title compound as an oil (23.6 g, 76%), b.p. 90°–92° C./0.2 mm.

(2) Diels-Alder reaction between maleinaldehydic acid psuedoethyl ester and cyclopentadiene Freshly cracked cyclopentadiene (9.0 g) is mixed with 11.9 g of the pseudo ester (1). A gentle warming is observed and the mixture is allowed to stand overnight. The n.m.r. spectrum typically shows the formation of the adduct (2) to be complete and the material is taken to the next step without purification.

(3)

5-endo-Ethoxycarbonyl-6-exo-diethoxymethyl-bicyclo [2,2,1] hept-2Z-ene

The Diels-Alder adduct (2) (10 g) is heated in a mixture of triethyl orthoformate (10 ml), dry ethanol (100 ml), and concentrated sulphuric acid (1 ml). The mixture darkens and after 12 hours is cooled and treated with anhydrous potassium carbonate (5 g) and ether (150 ml). Water is then slowly added with efficient mixing to neutralise the acid. The product is extracted with ether, washed with water and distilled to give the title compound as an oil (7.3 g, 63%), b.p. 115°–120° C./0.3 mm.

(4)

5-endo-Ethoxycarbonyl-6-exo-diethoxymethyl-bicyclo [2,2,1] heptane 5-endo-Ethoxycarbonyl-6-exo-diethoxymethyl-bicyclo [2,2,1] hept-2Z-ene(3) (30 g) is dissolved in 200 ml of ethanol and 0.3 g of 10% palladium on charcoal is added. The mixture is vigorously stirred in 1 atmosphere of hydrogen gas at room temperature. 1 molar equivalent of hydrogen gas is absorbed and the product is then isolated by removal of the catalyst by filtration through a Celite pad, followed by evaporation of the filtrate to give a quantitative yield of the title compound as an oil b.p. 105°–110° C./1.5 mm.

(5)
5-endo-Hydroxymethyl-6-exo-diethoxymethyl-bicyclo [2,2,1]heptane

The ester (4) (27 g) is added in ether to a 10% excess of lithium aluminium hydride (2.1 g) in ether with stirring at reflux temperature. The mixture is boiled for 1 hour after the addition and is then quenched by the addition of wet ether followed by 5% aqueous sodium hydroxide to precipitate aluminium salts. The colourless organic phase is dried over magnesium sulphate, filtered and evaporated to give the title compound as an oil (20 g, 91%).

(6) 5-endo-Cyanomethyl-6-exo-diethoxy-bicyclo [2,2,1] heptane

The alcohol (5) (20 g) in a minimum volume of dry pyridine is added slowly to 20 g of p-toluenesulphonyl chloride in 130 ml dry pyridine with stirring at 0° C. The mixture is kept at 5° C. overnight and then poured into a water-ice mixture. The resulting precipitate is filtered off and dried to give the tosylate ester of the alcohol in 85% yield as an off-white solid, m.p. 83°–86° C. (dec.).

The tosylate (14 g) in 15 ml dimethyl sulphoxide is added to 5 g of dry potassium cyanide in 20 ml dimethyl sulphoxide. The mixture is stirred under nitrogen and the temperature slowly raised over 1 hour to 110° C. After 5 hours the reaction mixture is cooled and poured into water. The product is isolated by ether extraction, and purified by distillation to give the title compound (7.8 g, 90%), b.p. 115°–126° C./1.5 mm.

(7)
6-exo-Diethoxymethyl-5-endo-formylmethyl-bicyclo [2,2,1] heptane

The cyano compound (6) (20 g) is stirred at −15° C. in 200 ml dry toluene under nitrogen. Diisobutylaluminium hydride (113 ml of a 1M solution in hexane) is added to the substrate over 25 minutes and the mixture allowed to reach room temperature. After 1 hour, methanol (30 ml) is cautiously added, followed by 400 ml of saturated aqueous sodium hydrogen tartrate. The mixture is stirred and heated at 40° C. for 2 hours. The upper organic layer is separated and the aqueous phase further extracted with ethyl acetate. The combined organic solutions are dried (MgSO$_4$) and the solvent removed to give a yellow oil. This is chromatographed on Florisil in benzene to give the pure title compound as a colourless oil (17.2 g, 85%), $\nu_{max}$ (film): 1725 cm$^{-1}$.

(8)
5-endo-(6'-Carboxyhex-2'Z-enyl)-6-exo-diethoxymethyl-bicyclo [2,2,1] heptane (4-Carboxy-n-butyl)-triphenylphosphonium bromide (23.3 g) is dried at 75° C. under vacuum for 2.5 hours. The resulting white solid is then cooled, the vacuum released to dry nitrogen, and 30 ml of dimethyl sulphoxide is added. A 2M solution of dimesyl sodium in dimethyl sulphoxide (50 ml) is added slowly while the mixture is maintained at 25° C. with a water bath. After 15 minutes the aldehyde (7) (5.0 g) is added to the deep red ylide thus produced. The mixture is stirred overnight and then the solvent is removed at 55°–60° C. under vacuum. The residue is dissolved in water, and the aqueous phase is extracted with ether and then carefully acidified to pH4 with 2N HCl. The precipitate is extracted into ether and the ethereal solution is dried and concentrated to give the title compound as an oil (3.7 g, 55%).

(9)
5-endo-(6'-Methoxycarbonylhex-2'Z-enyl)-6-exo-formyl-bicyclo [2,2,1] heptane The acid/acetal (8) (1.8 g) in ether is treated with an excess of ethereal diazomethane to form the methyl ester and then the acetal protecting group is removed by dissolving the compound in 200 ml chloroform and adding 50 ml of concentrated hydrochloric acid to form a two phase system. The mixture is vigorously stirred for 90 minutes and is then extracted with ether and the ethereal solution dried (MgSO$_4$) and concentrated to give the title compound as an oil.

Note: Care should be taken to avoid contact of this compound with methanol since it very readily forms a dimethyl acetal.

(10)
5-endo-(6'-Methoxycarbonylhex-2'Z-enyl)-6-exo-aminomethylbicyclo [2,2,1] heptane The ester/aldehyde (9) (2.5 g) and ammonium chloride (5.3 g, 10 equiv.) in 35 ml of 4:3 v/v methanol/water are stirred at room temperature for 15 minutes and sodium cyanoborohydride (0.5 g) is added in one portion. The mixture is stirred overnight and the pH is then adjusted to 2 with concentrated aqueous hydrochloric acid. After a further 30 minutes, neutral and acidic material is extracted with ether and the aqueous residue is then basified and again extracted with ether. This second ethereal extract is dried (MgSO$_4$) and evaporated to give the title compound as an oil in 73% yield, $\delta$(CDCl$_3$) 2.3 (2H, t), 2.25 (2H, br-s), 3.65 (3H, s), 5.35 (2H, m); mass spectroscopy on the product from treatment with N,O-bis-(trimethylsilyl)-trifluoroacetamide (BSTFA) shows peaks at 338, 323, 311 and 249.

EXAMPLE 2

5-endo-(6'-Carboxyhex-2'Z-enyl)-6-exo-[N-(phenylcarbamoyl)-aminomethyl]-bicyclo [2,2,1] heptane

(1)
5-endo-(6'-Methoxycarbonylhex-2'Z-enyl)-6-exo-[N-(phenylcarbamoyl)-aminomethyl]-bicyclo [2,2,1] heptane 5-endo-(6'-Methoxycarbonylhex-2'Z-enyl)-6-exo-aminomethylbicyclo [2,2,1] heptane (0.1 g; prepared as in Example 1) and phenyl isocyanate (1 equiv.) in dioxan (15 ml) are stirred for 5 minutes at room temperature. The solvent is removed in vacuo and the resultant product is purified by liquid-gel partition chromatography on a column of Sephadex LH20 (Pharmacia) substituted with Nedox 1114 olefin oxide to 50% w/w (Lipidex-Ashland Chemical Co. USA) and eluting with hexane/dichloroethane (90:10 v/v) to give the title compound as an oil in 94% yield, $\delta$(CDCl$_3$) 3.72 (3H, s), 5.42 (2H, m), 7.42 (5H, m), 7.2 (1H, br), 8.15 (1H, br).

(2)
5-endo-(6'-Carboxyhex-2'Z-enyl)-6-exo-[N-(phenylcarbamoyl)aminomethyl]-bicyclo [2,2,1] heptane The ester/urea (1) (90 mg) in aqueous methanol (10 ml) is treated with 1M methanolic potassium hydroxide (4 equiv.) and the mixture is heated at 35°–40° C. for 4 hours. The pH is adjusted to 7 with 2M aqueous hydrochloric acid and the mixture is evaporated to ¼ volume and partitioned between aqueous hydrochloric acid of pH 3 (20 ml) and ether (20 ml). The aqueous phase is extracted with ether (2×20 ml) and these extracts are combined with the original ethereal phase and dried (MgSO₄). The dried ethereal solution is filtered and evaporated to give a residue which is chromatographed on Sephadex LH20 substituted with Nedox 1114 olefin oxide to 27% w/w (Lipidex), eluting with dichloroethane hexane/ethanol/glacial acetic acid (100:100:5:0.1 by volume). Evaporation of the eluate gives the title compound as an oil (32 mg, 35%), $\lambda_{max}$ (CH₃OH) 240 and 273 nm, $\epsilon_{max}$21,090 and 1,300, $\delta$(CDCl₃) 5.40 (2H, m), 7.1 (1H, br), 7.35 (5H, m), 7.8 (2H, br), m/e 370, 119 (base peak).

EXAMPLE 3

5-endo-(6'-Methoxycarbonylhex-2'Z-enyl)-6-exo-aminomethyl-bicyclo [2,2,1] hept-2Z-ene (1), (2), (3)
5-endo-Ethoxycarbonyl-6-exo-diethoxymethyl-bicyclo [2,2,1]-hept-2Z-ene Maleinaldehydic acid pseudo-ethyl ester is prepared as described in Example 1(1) and reacted with cyclopentadiene in a Diels-Alder reaction as described in Example 1(2). The Diels-Alder adduct is treated with ethanol under acidic conditions as described in Example 1(3) to give 5-endo-ethoxycarbonyl-6-exo-diethoxymethyl-bicyclo [2,2,1] hept-2Z-ene (3).

(4)
5-endo-Hydroxymethyl-6-exo-diethoxymethyl-bicyclo [2,2,1] hept-2Z-ene

The ester (3) is added in ether to lithium aluminium hydride (10% excess) in ether with stirring at reflux temperature. After the addition, the mixture is boiled for a further 1 hour. The reaction is quenched with wet ether and then 5% aqueous sodium hydroxide to precipitate aluminium. The colourless organic phase is filtered, dried over anhydrous potassium carbonate, and the resulting alcohol (85–90% yield) used directly in the next stage.

(5) 5-endo-Cyanomethyl-6-exo-diethoxymethyl-bicyclo [2,2,1] hept-2Z-ene

The alcohol (4) (7 g) in 15 ml dry pyridine is added slowly at 0° C. to p-toluenesulphonyl chloride (7.5 g) in pyridine (45 ml). The mixture is kept overnight at 10° C. and then quenched by pouring over ice with vigorous shaking. The product is extracted with ether, washed consecutively with water, 0.1M sodium carbonate and brine, and then dried (K₂CO₃) and the solvent removed to give the tosylate ester of the alcohol as a colourless oil in high yield.

The tosylate ester (12 g) in dimethyl sulphoxide (15 ml) is added with stirring to potassium cyanide (3 g) in dimethyl sulphoxide (20 ml). The mixture is heated to 100° C. under nitrogen for 6 hours and is then cooled, poured into water and the product taken into ether. The solvent is removed and the residue distilled to give title compound as an oil (6.6 g, 88%), b.p. 112°–124° C./1.8 mm.

(6)
6-exo-Diethoxymethyl-5-endo-formylmethyl-bicyclo [2,2,1] hept-2Z-ene

Di-isobutylaluminium hydride (25 ml of 1M solution in hexane) is added with stirring over a 10 minute period to the cyano compound (5) (5.0 g) in dry toluene (70 ml) at −15° C. under nitrogen. After a further 1 hour at room temperature the reaction is terminated by the additon with caution of methanol (6 ml), followed by saturated aqueous sodium hydrogen tartrate (95 ml). The mixture is then stirred and heated at 40° C. for 2 hours. The organic phase is separated and the aqueous layer is further extracted with ethyl acetate, the combined organic solutions being dried and stripped of solvent to give the product as a yellow oil. Chromatography on Florisil (trade name) in benzene gives the pure title compound as a colourless oil (3.2 g, 63%) $v_{max}$(film): 1725 cm⁻¹.

(7)
5-endo-Carboxyhex-2'Z-enyl-6-exo-diethoxymethyl-bicyclo [2,2,1] hept-2Z-ene (4-Carboxy-n-butyl)-triphenylphosphonium bromide (7.0 g) is dried at 75° C. under vacuum for 90 minutes. The white solid is cooled, the vacuum is released to dry nitrogen and 10 ml of dimethyl sulphoxide is added followed by 15 ml of a 2M solution of dimesyl sodium in dimethyl sulphoxide. The temperature is maintained at 25° C. and the aldehyde (6) (1.5 g) is added to the deep red yield solution. After stirring overnight the solvent is removed at 55°–60° C. under vacuum. The residue is dissolved in water, extracted with ether, and the aqueous phase carefully acidified to pH4 with 2N HCl. The mixture is extracted with ether and the ethereal solution dried and concentrated to give the title compound as an oil (1.34 g, 66%).

(8)
5-endo-(6'-Methoxycarbonylhex-2'Z-enyl)-6-exo-formyl-bicyclo [2,2,1] hept-2Z-ene The acid/acetal (7) (5 g) in ether is treated with excess ethereal diazomethane to form the methyl ester and then the ketal protecting group is removed by dissolving the compound in 215 ml chloroform and adding concentrated hydrochloric acid (55 ml) to form a two-phase system. The mixture is extracted with ether and the ethereal solution dried and concentrated to give the title compound as an oil (3.38 g, 90%).

Note: Care should be taken to avoid contact of this compound with methanol since it very readily forms the dimethyl acetal.

(9)
5-endo-(6'-Methoxycarbonyl-2'Z-enyl)-6-exo-aminomethyl-bicyclo [2,2,1] hept-2Z-ene To a solution of the ester/aldehyde (8) (0.850 g, 3.25 mmol) in methanol (45 ml) is added ammonium acetate (1.8 g) and the mixture is stirred for 15 minutes at room temperature. Sodium cyanoborohydride (150 mg, 2.5 mmol) is added and stirring continued for 4 hours at room temperature. 12M aqueous hydrochloric acid (2 ml) is then added and the acidified mixture stirred for a further ½ hour. The mixture is evaporated to ¼ volume, water (20 ml) is added and the solution is extracted with ether (25 ml). The aqueous phase is brought to pH 10 by the addition of solid potassium hydroxide, saturated with solid sodium chloride and extracted with ether (3×25 ml). The combined extracts are dried (MgSO₄), filtered and evaporated to give the title compound as a colourless oil (192 mg, 23%), $v_{max}$ (film) 3,300 cm⁻¹, $\delta$(CDCl₃) 1.00 (2H, br), 3.70 (3H, s), 5.50 (2H, m), 6.10 and 6.30 (2×1H, dd), m/e (on compound silylated with BSTFA) 339.

EXAMPLE 4

5-endo-(6'-Methoxycarbonylhex-2'Z-enyl)-6-exo(2'-aminoethyl)-bicyclo [2,2,1] hept-2Z-ene

(1)
5-endo-(6'-Methoxycarbonylhex-2'Z-enyl)-6-exo-(2'-nitroethyl)-bicyclo [2,2,1] hept-2Z-ene To a solution of 5-endo-(6'-Methoxycarbonylhex-2'Z-enyl)-6-exoformyl-bicyclo [2,2,1] hept-2Z-ene [1.0 g, 3.8 mmol, prepared as in Example 3(8)] in isopropanol (30 ml), is added nitromethane (1 ml, 1.0 g, 15 mmol) and anhydrous potassium fluoride (20 mg) and the mixture is stirred at room temperature for 18 hours. The solvent is removed in vacuo, the resultant crude ester/nitro-alcohol is dissolved in dichloromethane (30 ml), 4-dimethylaminopyridine (20 mg) and acetic anhydride (0.5 ml, 5 mmol, 1.3 equiv.) are added and the mixture is then stirred for 2 hours at room temperature. The solvent is removed in vacuo and the resultant crude ester/nitro-acetate is dissolved in tetrahydrofuran (30 ml). Sodium borohydride (300 mg, 8 mmol, 2 equiv.) is added to the solution and the mixture is stirred at 0° C. for ½ hour. Water (20 ml) is then added and the mixture stirred for a further 10 minutes. The mixture is extracted with ether (2×25 ml), dried (MgSO₄), filtered and evaporated to give a yellow oil. Chromatography of this oil on Florisil (20 g) in toluene as eluant gives the title compound as an oil (916 mg, 78%), $\nu_{max}$(film) 1545 cm$^{-1}$, $\delta$(CDCl$_3$) 3.66 (3H, s), 4.43 (2H, t, J 7.5Hz), 5.4 (2H, m), 6.1 (2H, m), m/e 307,241.

(2)
5-endo-(6'-Methoxycarbonylhex-2'Z-enyl)-6-exo-formylmethyl-bicyclo [2,2,1] hept-2Z-ene The nitro/ester (1) (555 mg, 1.9 mmol) is dissolved in 5M methanolic sodium methoxide solution (5 ml, 2.5 mmol) and added dropwise during 5 minutes to a solution of sulphuric acid (98%, 4 ml) in methanol (20 ml) at −45° C. Dichloromethane (50 ml) is added, the mixture is washed with aqueous sodium hydroxide solution (5M, 50 ml) and then water (50 ml), dried (MgSO₄), filtered and evaporated to give the dimethyl acetal of the title compound as a colourless oil (547 mg, 94%), $\delta$(CDCl$_3$) 3.67 (3H, s), 4.46 (1H, t, 5.5Hz), 5.43 (2H, m), 6.10 (2H, lm), 7.32 and 7.34 (2×3H, s). The crude acetal is dissolved in dichloromethane (10 ml), 12M aqueous hydrochloric acid (2 ml) is added and the mixture is stirred for ½ hour at room temperature. The organic portion of the mixture is then separated, dried (K₂CO₃), filtered and evaporated. The resultant residue is chromatographed on Florisil (15 g) in toluene, using 5% v/v ether in toluene to elute the title compound which is obtained on evaporation as an oil (0.348 g, 70%), $\nu_{max}$ (film) 1715 cm$^{-1}$, $\delta$(CDCl$_3$) 3.68 (3H, s), 5.38 (2H, m), 6.13 (2H, m), 9.75 (1H, t), m/e 276.

(3)
5-endo-(6'-Methoxycarbonylhex-2'Z-enyl)-6-exo-(2'--aminoethyl)-bicyclo [2,2,1] hept-2Z-ene To a solution of the ester/aldehyde (2) (264 mg, 1 mmol) in tetrahydrofuran (30 ml) is added water (5 ml), methanol (10 ml) and ammonium chloride (2 g). After stirring for 10 minutes, sodium cyanoborohydride (250 mg) is added and the mixture stirred at room temperature for a further 1 hour. Aqueous hydrochloric acid (12M, 0.5 ml) is then added and stirring continued for ½ hour. The mixture is evaporated to ¼ volume, water (20 ml) is added and the resultant product is extracted with ether (30 ml). The aqueous phase remaining after the extraction is brought to pH 10 by the addition of solid potassium hydroxide, saturated with sodium chloride, and re-extracted with ether (3×30 ml). The extracts are dried (MgSO₄), filtered and evaporated to give the title compound as a colourless oil (77 mg, 29%), $\nu_{max}$ 3,300 cm$^{-1}$, $\delta$(CDCl$_3$) 3.69 (3H, s), 5.40 (2H, m), 6.10 (2H, m), m/e 349.

EXAMPLE 5

5-endo-(6'-Methoxycarbonylhex-2'Z-enyl)-6-exo-(2'-aminopropyl)-bicyclo [2,2,1] hept-2Z-ene

(1)
5-endo-(6'-Methoxycarbonylhex-2'Z-enyl)-6-exo-(2'-nitropropyl)-bicyclo [2,2,1] hept-2Z-ene To a solution of 5-endo-(6'-methoxycarbonylhex-2'Z-enyl)-6-exo-formyl-bicyclo [2,2,1] hept-2Z-ene [1.047 g, 4 mmol, prepared as in Example 3(8)] in propan-2-ol (20 ml), is added potassium fluoride (20 mg) and nitroethane (3 g), and the mixture is stirred for 48 hours at room temperature. The mixture is then evaporated to dryness and the resultant residue is suspended in dichloromethane (20 ml). To the suspension are added 4-dimethylaminopyridine (20 mg) and acetic anhydride (2 g), and the mixture is stirred for 16 hours at room temperature. The solvent is evaporated, the resultant residue is suspended in toluene (10 ml), and the suspension is cooled to 0° C. and then treated with diazabicycloundecene (0.76 g, 5 mmol). After stirring for 10 minutes, the mixture is washed with water (20 ml), 0.5M aqueous hydrochloric acid (20 ml), saturated aqueous sodium hydrogen carbonate solution (20 ml) and finally water (20 ml), then dried (MgSO₄), filtered and evaporated to give the resultant crude ester/nitro-olefin as a pale yellow oil (1.2 g).

The crude ester/nitro-olefin is immediately dissolved in tetrahydrofuran (15 ml), cooled to 0° C. and treated with sodium borohydride (150 mg), 2M aqueous hydrochloric acid being added dropwise to maintain a pH of 6–8. After stirring for 1 hour, ether (15 ml) and water (20 ml) are added with caution and the resultant mixture is then separated. The aqueous phase is extracted with ether (15 ml) and this extract is combined with the original etheral phase, dried (MgSO₄), filtered and evaporated to give the title compound as a pale yellow oil (0.937 g, 73%), $\nu_{max}$ (film) 1540 cm$^{-1}$, $\delta$(CDCl$_3$) 1.54 (3H, d, J=6Hz), 3.67 (3H, s), 4.65 (1H, m), 5.40 (2H, m), 6.1 (2H, m), m/e 321.

(2)
5-endo-(6'-Carbomethoxyhex-2'Z-enyl)-6-exo-acetonyl-bicyclo [2,2,1] hept-2Z-ene A solution of the nitro-ester (1) (0.937 g, 2.9 mmol) in sodium methoxide solution (0.5M, 10 ml) is added dropwise during 10 minutes to stirred solution of sulphuric acid (4 ml) in methanol (20 ml) at −40° C. and the resultant mixture is allowed to warm to room temperature during ½ hour. The mixture is washed with 5M aqueous sodium hydroxide solution (50 ml) and water (50 ml), dried (MgSO₄), filtered and evaporated. The residue is chromatographed on Florisil (20 g) in toluene using a gradient of 0–10% v/v of ether in toluene to elute the title compound which is obtained on evaporation as an oil (0.578 g, 68%), $\nu_{max}$ 1720 cm$^{-1}$, $\delta$(CDCl$_3$), 2.15 (3H, s), 3.68 (3H, s), 5.38 (2H, m), 6.02 and 6.25 (2×1H, dd), m/e 290.

(3)

5-endo-(6'-Methoxycarbonylhex-2Z-enyl)-6-exo-(2'-aminopropyl)-bicyclo [2,2,1] hept-2Z-ene

The solution of the ester/ketone (2) (326 mg, 1.1 mmol) in methanol (20 ml) is added ammonium acetate (1.0 g) and 3A molecular sieves (2 g), and the mixture is stirred for 15 minutes. Sodium cyanoborohydride (100 mg) is added and the stirring continued for 24 hours at room temperature. The mixture is filtered, 12M aqueous hydrochloric acid (2 ml) is added to the filtrate, and is then evaporated to ¼ volume and partitioned between water (20 ml) and ether (20 ml). The aqueous phase is brought to pH 10 by the addition of solid potassium hydroxide, saturated with solid sodium chloride and then extracted with ether (4×20 ml). The combined extracts are dried (MgSO$_4$), filtered and evaporated to give the title compound as a colourless oil (195 mg, 60%), $\nu_{max}$ 3,300 cm$^{-1}$, δ(CDCl$_3$) 1.09 (3H, d, J=7Hz), 3.01 (1H, q, J=7Hz), 3.69 (3H, s), 5.43 (2H, m), 6.03 and 6.25 (2×1H, dd).

EXAMPLE 6

5-endo-(6'-Methoxycarbonylhex-2'Z-enyl)-6-exo-(2'-diphenylmethylaminopropyl)-bicyclo [2,2,1] hept-2Z-ene

To a solution of 5-endo-(6'-methoxycarbonyl-2'Z-enyl)-6-exo-(2'-aminopropyl)-bicyclo [2,2,1] heptane [57 mg, 0.2 mmol prepared as in Example 5(3)] in dichloromethane (4 ml), is added 4-dimethylamino-pyridine (10 mg), triethylamine (100 mg) and bromodiphenylmethane (250 mg, 1 mmol) and the resultant mixture is maintained at room temperature for 1 week. The solvent is then removed in vacuo and the residue is partitioned between water (20 ml) and ether (20 ml). The organic phase is dried (MgSO$_4$), filtered, evaporated and the residue chromatographed on Florisil (10 g) in toluene, using a gradient of 20–30% v/v ether in toluene to elute the title compound which is obtained on evaporation as a colourless oil (48 mg, 54%), δ(CDCl$_3$) 1.08 (3H, d, J=7Hz), 3.63 (3H, s), 4.98 (1H, s), 5.30 (2H, m), 5.96 (1H, m), 6.16 (1H, m), 7.27 (10H, m).

EXAMPLE 7

Preparation of carbamoyl and thiocarbomoyl derivatives of amines

To a solution of an amine of the formula (II) shown hereinbefore containing a group —A—NHR$^2$ (about 0.5 mmol) in dioxan (10 ml) is added an isocyanate R$^4$NCO or thioisocyanate R$^4$NCS (1.2 equiv.) and the solution is stirred at room temperature for 10 minutes. The solvent is removed in vacuo and the product is chromatographed on Florisil (5 g) in toluene using a gradient of 0% to 100% v/v ether in toluene to elute the carbamoyl or thiocarbamoyl derivative of formula

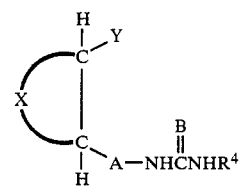

wherein B represents an oxygen or sulphur atom and the other symbols are as defined for formula (I) but with the letters a and b relating instead to the substituents Y and A—NHCBNHR$^4$, respectively, the derivative being isolated in pure form by evaporation of the solvent from the eluate.

This procedure is used to prepare the p-methoxyphenylcarbomoyl and p-methoxyphenylthiocarbamoyl derivatives of the amine of Example 3, and the phenylcarbamoyl, p-methoxyphenylcarbamoyl and p-methoxyphenylthiocarbamoyl derivatives of the amines of Examples 4 and 5. The details of these preparations are given in Table 1 below whilst the n.m.r data for the products obtained is given in Table 2 below (as usual this data relates to values in p.p.m. obtained in CDCl$_3$ solution and referred to TMS. In each case the divalent cyclic group derives from a 5-endo, 6-exo substituted bicyclo [2,2,1 hept-2Z-ene ring system and the substitutent Y is a 6-methoxycarbonylhex-2Z-enyl group so that the various products are identified only by the nature of the substituent A—NHCBNHR$^4$ which they contain

TABLE 1

| Number | Product —ANHCBNHR$^4$ | Starting material/ product (mg/mg) | Yield (%) |
|---|---|---|---|
| 1 | —CH$_2$NHCONHC$_6$H$_4$OCH$_3$(p) | 92/149 | 98 |
| 2 | —CH$_2$NHCSNHC$_6$H$_4$OCH$_3$(p) | 100/157 | 97 |
| 3 | —(CH$_2$)$_2$NHCONHC$_6$H$_5$ | 73/82 | 82 |
| 4 | —(CH$_2$)$_2$NHCONHC$_6$H$_4$OCH$_3$(p) | 120/133 | 98 |
| 5 | —(CH$_2$)$_2$NHCSNHC$_6$H$_4$OCH$_3$(p) | 77/61 | 60 |
| 6 | —CH$_2$CH(CH$_3$)NHCONHC$_6$H$_5$ | 90/115 | 91 |
| 7 | —CH$_2$CH(CH$_3$)NHCONHC$_6$H$_4$OCH$_3$(p) | 91/138 | 100 |
| 8 | —CH$_2$CH(CH$_3$)NHCSNHC$_6$H$_4$OCH$_3$(p) | 90/129 | 98 |

TABLE 2

| Compound Number | Protons of —CO$_2$CH$_3$ | Protons of para —OCH$_3$ | Olefinic protons of Y | Olefinic protons of X | Aromatic protons | NH protons —A—NHCBNHR$^4$ |
|---|---|---|---|---|---|---|
| 1 | 3.66 | 3.76 | 5.40 | 6.15 | 6.85 7.20 | 6.65 7.80 |
| 2 | 3.67 | 3.79 | 5.45 | 6.12 | 6.85 7.25 | 6.30 7.30 |
| 3 | 3.69 | — | 5.40 | 6.11 | 7.32 | 5.67 7.69 |
| 4 | 3.67 | 3.79 | 5.38 | 6.10 | 7.21 | 6.90 8.30$^{(1)}$ |
| 5 | 3.65 | 3.82 | 5.35 | 6.08 | 6.90 7.20 | 5.82 7.75 |
| 6 | 3.65 | — | 5.32 | 6.05 | 7.14 | 5.57 8.30 |
| 7 | 3.66 | 3.72 | 5.29 | 6.00 | 6.99 | 7.1–7.3 |

TABLE 2-continued

| Compound Number | Protons of $-CO_2CH_3$ | Protons of para $-OCH_3$ | Olefinic protons of Y | Olefinic protons of X | Aromatic protons | NH protons $-A-NHCBNHR^4$ |
|---|---|---|---|---|---|---|
| 8 | 3.68 | 3.84 | 5.47 | 6.11 | 7.08 | 5.65 8.27 |

[1]assignment not fully clear.

(1) assignment not fully clear.

EXAMPLE 8

Preparation of free acids from carbamoyl and thiocarbamoyl amine derivatives in ester form To a solution of a carbamoylamine or thiocarbamoylamine derivative of formula

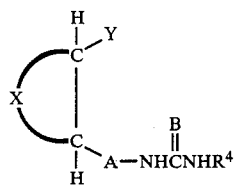

wherein B represents an oxygen or sulphur atom and the other symbols are as defined for formula (1) but with Y being a 6-carboxyhex-2Z-enyl group or a modification thereof of type (a), (b), (c) or (d) in the form of an ester derivative of the carboxy group and the letters a and b relating instead to the substituents Y and $A-NHCBNHR^4$, respectively, in aqueous methanolic solution (2:3 v/v of $H_2O:CH_3OH$) is added an excess (about 4 equiv.) of a 1M methanolic solution of potassium hydroxide and the mixture is heated at 35°–40° C. for 4 hours. 2M aqueous hydrochloric acid is added to adjust the pH of the mixture to 7 and it is then evaporated to ¼ volume and partitioned between aqueous hydrochloric acid of pH 3 (20 ml) and ether (20 ml). The aqueous phase is extracted (2×20 ml) with ether and these extracts are combined with the original ethereal phase, dried ($MgSO_4$), filtered and evaporated. The residue is chromatographed using a LH20 Sephadex column substituted with Nedox 1114 olefin oxide to 20% or 27% w/w (Lipidex) with a mixture of 1,2-dichloroethane, hexane, ethanol and glacial acetic acid as eluant. The free acid is isolated in pure form by evaporation of the solvent from the eluate.

This procedure is applied to the esters listed in Table 1 of Example 7 to prepare the corresponding free acids. The details of these preparations are given in Table 3 below whilst the u.v., m.s and n.m.r data for the products (the n.m.r. data being obtained as indicated for Table 2) is given in Tables 4 and 5 below, the various products being identified as in Table 1 by the nature of the substituent $A-NHCBNHR^4$ which they contain.

TABLE 3

| Product[1] Number | Starting material/ Product (mg/mg) | Yield (%) | Eluant $CH_2Cl_2:C_6H_{12}:C_2H_5OH:CH_3CO_2H$ by volume |
|---|---|---|---|
| 1' | 90/32 | 35 | 100:100:5:01 |
| 2' | 157/36 | 24 | 100:100:5:01 |
| 3' | 82/51 | 66 | 100:100:5:01[2] |
| 4' | 52/16 | 33 | 100:100:2:01 |
| 5' | 61[3] | — | 100:100:1:01 |
| 6' | 115[3] | — | 100:100:2:01 |
| 7' | 138[3] | — | 100:100:2:01 |
| 8' | 129/112 | 90 | 100:100:2:01 |

[1]Each product is obtained from the corresponding ester identified in Table 1 by the same number but lacking the prime, i.e. the ester 1 of Table 1 yields the acid 1' of Table 2.
[2]In this case the level of substitution of the LH20 Sephadex with Nedox 1114 olefin oxide is 20% w/w; in all other cases it is 27%.
[3]Amount of product obtained not recorded.

TABLE 4

| Compound Number | U.V. Data ($CH_3OH$) | | M.S. Data | |
|---|---|---|---|---|
| | $\gamma_{max}$(nm) | $\epsilon_{max}$ | $M^+$ | base peak[1] |
| 1' | 243 284 | 10,550 1,190 | (2) | |
| 2' | 247 | 14,070 | absent | 165 |
| 3' | 240 273 | 21,010 1,330 | 382 | 119 |
| 4' | 243 290 | 17,720 1,650 | 412 | 149 |
| 5' | 247 | 15,830 | absent | 165 |
| 6' | 240 273 | 22,180 1,980 | 396 | 119 |
| 7' | 243 289 | 16,250 1,400 | (2) | |
| 8' | 247 | 15,880 | absent | 165 |

[1]The base peak corresponds to a fragment which is the isocyanate or thioisocyanate used in the preparation of the equivalent ester of Example 7.
[2]Mass spectrum not recorded.

TABLE 5

| Compound Number | Protons of para $-OCH_3$ | Olefinic protons of Y | Olefinic protons of X | Aromatic protons | NH and OH protons $-A-NHCBNHR^4$ $-CO_2H$ | | |
|---|---|---|---|---|---|---|---|
| 1' | 3.76 | 5.39 | 6.10 | 6.95 7.35 | 6.40 | 8.33 | 8.70 |
| 2' | 3.84 | 5.30 | 6.10 | 6.90 7.30 | 6.45 | | 8.2 |
| 3' | — | 5.30 | 6.05 | 7.13 | 5.52 | | 8.1 |
| 4' | 3.82 | 5.42 | 6.12 | 7.20 | 6.90 | 8.30 | 8.45 |
| 5' | 3.76 | 5.32 | 6.00 | 7.00 | 5.75 | 7.70 | 9.70 |
| 6' | — | 5.33 | 6.04 | 7.20 | 7.05 | 7.90 | 8.20 |
| 7' | 3.82 | 5.32 | 6.02 | 6.75 7.15 | 6.95 | 8.35 | 9.05 |
| 8' | 3.85 | 5.35 | 6.13 | 7.10 | 5.70 | 8.40 | 9.40 |

EXAMPLE 9

Tests of biological activity

The compound of Example 2 and various of the compounds of Example 8 are tested in the following three systems.

Rabbit Aorta System

Sprial strips of thoracic aorta are suspended in Kreb's-Henseleit solution aerated with 95% $O_2$/5% $CO_2$ and maintained at 37° C. Tension changes are recorded with a Grass FTO3 force transducer. Initially, cumulative dose response curves to the agonist 11,9-(epoxymethano) PGH₂ are obtained (typically at concentrations of $2\times10^{-9}$, $1\times10^{-8}$, $5\times10^{-8}$ and $2.5\times10^{-7}$M). In a second experiment, the compound under test is added 50 minutes previous to the addition of the series of agonist doses.

Guinea Pig Trachea System

Spiral strips of trachea are suspended in Kreb's-Henseleit solution, additionally containing atropine sulphate ($2\times10^{-8}$M) and indomethacin ($10^{-6}$M), aerated with 95% O₂/5% CO₂ and maintained at 37° C. Tension changes are recorded with a Grass FTO3 force transducer. Initially, cumulative dose response curves to the agonist 11,9-(epoxymethano) PGH₂ are obtained (typically at the same concentrations as for the rabbit aorta system). In a second experiment, the compound under test is added 50 minutes previous to the addition of the series of agonist doses.

Human Platelet System

Platelet-rich plasma is obtained from fresh, citrated human blood. Addition of the agonist 11,9-(epoxymethano) PGH₂ ($1\times10^{-7}$ to $5\times10^{-7}$M) causes immediate aggregation recorded as an increase in light transmission (600 nm). In a second experiment the compound under test is added 5 minutes previous to the addition of the PGH₂ analogue. The dose of the PGH₂ analogue added is then increased to a level which gives a similar response to that obtained in the absence of antagonist.

In the case of each system, the affinity constant, $K_B$, for the compound under test is calculated according to the Gaddum-Schild Equation (based on Law of Mass Action).

$$DR - 1 = [B] \times K_B$$

DR = dose ratio
[B] = molar concentration of compound

Typical values of the affinity constants obtained in these systems for the various compounds tested are given in Table 6 below.

TABLE 6

| Compound[1] —ANHCBNHR⁴ | Affinity Constants ($K_B$) $\times 10^{-6}$(M$^{-1}$) | | |
|---|---|---|---|
| | Rabbit Aorta | Guinea Pig Trachea | Human Platelets |
| —CH₂NHCONHC₆H₅ | 1.0 | 3.1 | 0.28 |
| —CH₂NHCSNHC₆H₄OCH₃(p) | 5.9 | 6.5 | 0.072 |
| —(CH₂)₂NHCONHC₆H₅ | 2.9 | 5.1 | 0.034 |
| —(CH₂)₂NHCONHC₆H₄OCH₃(p) | 1.2 | 6.9 | — |
| —(CH₂)₂NHCSNHC₆H₄OCH₃(p) | 1.9 | — | 0.080 |
| —CH₂CH(CH₃)NHCOC₆H₅ | 0.9 | 2.2 | — |
| —CH₂CH(CH₃)NHCSNHC₆H₄OCH₃(p) | 0.95 | 8.1 | 0.20 |

[1]Each compound is a bicyclo [2,2,1] hept-2Z-ene, except for the first which is a bicyclo [2,2,1] heptane, and all are substituted at the 5-position by a 6-carboxyhex-2Z-enyl group and at the 6-position by a group —ANHCBNHR⁴ as shown.

We claim:
1. A compound of formula (I)

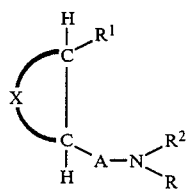

(I)

wherein

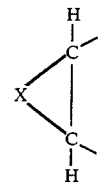

represents one of the cyclic groups shown below:

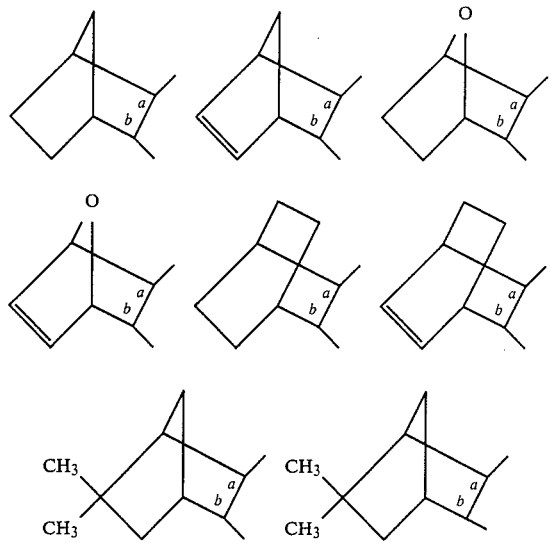

the letters a and b indicating in each case the points of attachment of the substituents R¹ and A—NR²R, respectively; R¹ is a 6-carboxyhex-2-enyl group, or a modification thereof in which the group is altered by one, or an appropriate combination of two or more, of the following: (a) alteration of the position of the double bond from the 2,3-position to the 3,4-position, (b) reduction of the double bond, (c) replacement of a methylene group at position 2 or 3 by an oxygen or sulphur atom in conjunction with reduction of the double bond, (d) alteration of the chain length through a decrease or an increase of one or two methylene groups, and (e) formation of a derivative of the carboxy group in the form of a pharmaceutically acceptable salt, C₁₋₁₀ alkyl ester or an amide containing a group —CONH₂ or such a group in which the nitrogen atom is substituted by one or two groups selected from C₁₋₁₀ alkyl groups, phenyl and phenyl substituted by one or more substituents selected from $C_{1-10}$ alkoxy, halogen, $C_{1-10}$ halogen-substituted alkyl, sulfamyl, amino, hydroxyl, nitro and $C_{1-10}$ alkyl groups, or by one group —$SO_2R^6$ in which $R^6$ is a $C_{1-10}$ alkyl group; A is an aliphatic $C_{1-10}$ hydrocarbon group with a chain length between the points of attachment to the divalent cyclic group and to the group $NR^2R$ of 1 to 5 carbon atoms or such a group substituted by a group Ar, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulfamyl, amino, hydroxyl, nitro and $C_{1-10}$ alkyl groups; and $R^2$ is hydrogen, a $C_{1-10}$ aliphatic hydrocarbon group, a group Ar or a $C_{1-10}$ aliphatic hydrocarbon group substituted by one or more groups Ar; and R is a group —$CO.NR^3R^4$, —$CS.NR^3R^4$, —$CNH.NR^3R^4$ $CO.R^4$ or —$CS.R^4$ in which $R^3$ is hydrogen, A $C_{1-10}$ aliphatic hydrocarbon group, a group AR or a $C_{1-10}$ aliphatic hydrocarbon group, a group Ar or a $C_{1-10}$ aliphatic hydrocarbon group substituted by one or more groups Ar, but with the proviso that both $R^2$ and $R^3$ may not be other than hydrogen, and $R^4$ is a $C_{1-10}$ aliphatic hydrocarbon group, a group Ar or a $C_{1-10}$ aliphatic hydrocarbon group substituted by one or more groups Ar and/or by a group OAr, SAr, $OR^5$ or $SR^5$ wherein $R^5$ is a $C_{1-10}$ aliphatic hydrocarbon group substituted by one or more groups Ar.

2. A compound according to claim 1, which contains a bicyclo[2,2,2]octane or bicyclo[2,2,2]oct-2Z-ene ring system.

3. A compound according to claim 1, which contains a 6,6-dimethyl-bicyclo[3,1,1] heptane ring system having the group $R^1$ at the 3-position.

4. A compound according to claim 1, in which any modification of the 6-carboxyhex-2-enyl group of type (d) is a shortening or lengthening of the carbon chain by one methylene group.

5. A compound according to claim 1, in which $R^1$ is a 6-carboxyhex-2Z-enyl group or a derivative thereof formed at the carboxy group.

6. A compound according to claim 1, in which $R^1$ is a 6-carboxyhexyl group or a derivative thereof formed at the carboxy group.

7. A compound according to claim 1, in which $R^1$ is a group terminating in a free carboxy group or an ester derivative of the carboxy group.

8. A compound according to claim 1, in which any group A which is an aliphatic hydrocarbon group substituted by an aromatic group contains the aromatic substituent on a carbon atom in a branch from the chain of carbon atoms linking the divalent cyclic group and the group $NR^2R$, said branch being formed at the carbon atom of the chain which is bonded to the divalent cyclic group.

9. A compound according to claim 1, in which A has a chain length of 1 to 3 carbon atoms.

10. A compound according to claim 1, in which A is an unbranched or branched acyclic aliphatic hydrocarbon group.

11. A compound according to claim 10, in which A is an alkylene group with a chain length of 1 to 3 carbon atoms and an overall size of 1 to 5 carbon atoms.

12. A compound according to claim 11, in which A is a group —$CH_2$—, —$CH_2CH_2$—, —$CH(CH_3)$—, —$CH(CH_3)CH_3$—, —$CH_2CH(CH_3)$— or —$CH_2CH_2CH_2$—.

13. A compound according to claim 1, in which $R^2$ is hydrogen.

14. A compound according to claim 1, in which $R^2$ is a $C_{1-3}$ alkyl group.

15. A compound according to claim 1, in which R is a group —$CO.NR^3R^4$ or —$CS.NR^3R^4$.

16. A compound according to claim 1, in which $R^3$ is hydrogen.

17. A compound according to claim 1, in which $R^4$ is an unsubstituted alkyl group of 1 to 10 carbon atoms.

18. A compound according to claim 1, in which $R^4$ is an alkyl group of 1 to 3 carbon atoms substituted by one or more groups Ar.

19. A compound according to claim 1, in which $R^4$ is a group Ar.

20. A compound according to claim 18, in which Ar is selected from unsubstituted and substituted phenyl and pyridyl groups.

21. A compound according to claim 19, in which Ar is selected from unsubstituted and substituted phenyl and pyridyl groups.

22. A compound according to claim 1, in which Ar is selected from unsubstituted and substituted phenyl groups.

23. A compound according to claim 22, in which each group Ar is a phenyl group.

24. A compound according to claim 22, in which the substituted phenyl groups have a single substituent at an ortho, meta or para position or two identical substituents at any combination of ortho, meta and para positions.

25. A compound according to claim 23, in which one of the two substituents is at the para position.

26. A compound according to claim 1, which contains a bicyclo[2,2,2]octane or bicyclo[2,2,2] oct-2Z-ene ring system, and in which A is an alkylene group with a chain length of 1 to 3 atoms and an overall size of 1 to 5 carbon atoms and $NR^2R$ is a group —NH.CO.$NHR^4$ or —NH.CS.$NHR^4$, wherein $R^4$ is selected from unsubstituted phenyl, pyrid-2-yl, pyrid-3-yl and pyrid-4-yl groups, and substituted phenyl groups.

27. A compound according to claim 26, in which $R^4$ is selected from an unsubstituted phenyl group and substituted phenyl groups containing one or more substiuent groups selected from $C_{1-3}$ alkoxy, halogen, $C_{1-3}$ halogen-substituted alkyl and $C_{1-3}$ alkyl groups.

28. A compound according to claim 27, in which the substuent groups are selected from methyl, methoxy, fluoro, chloro, bromo and trifuoromethyl.

29. A compound according to claim 28, in which the substituent groups are methoxy.

30. A compound according to claim 1, in which the configuration about any double bond in the group $R^1$ is cis.

31. A compound according to claim 1, in which the groups $R^1$ and $ANR^2R$ are in a trans relationship.

32. A compound according to claim 1, being a bicyclo[2,2,2]octane of bicyclo[2,2,2]oct-2Z-ene having a 5-endo substituent which is a 6-carboxyhex-2Z-enyl or 6-carboxyhexyl group or a pharmaceutically acceptable amide, ester or salt derivative thereof and a 6-exo substituent which is an aminomethyl, 2-aminoethyl, 1-aminoethyl, 2-amino-1-methylethyl, 2-aminopropyl or 3-aminopropyl group that is itself N-substituted by a phenylcarbamoyl, p-methoxyphenylcarbamoyl, phenyl-thiocarbamoyl or p-methoxyphenylthiocarbamoyl group.

33. A pharmaceutical composition comprising a compound according to claim 1 as an active ingredient thereof for the treatment of thrombotic disorders, anaphylactic disease states and conditions requiring anti-inflammatory treatment, in combination with a physiologically acceptable diluent or carrier.

34. A method for treating thrombotic disorders, anaphylactic disease states and conditions requiring anti-inflammatory treatment in patients, which comprises administering to the said patient an amount of a compound according to claim 1 effective to inhibit thromboxane activity in the patient.

35. A compound according to claim 31, in which the divalent cyclic group has the 5-endo, 6-exo configuration when it is a bicyclo[2,2,2]oct-2Z-ene, and the 2α, 3β, 6α configuration when it is a 6,6-dimethylbicyclo[3,1,1]heptane.

36. A compound according to claim 1, which contains a 6,6-dimethyl-bicyclo[3,1,1] heptane ring system, and in which A is an alkylene group with a chain length of 1 to 3 carbon atoms and overall size of 1 to 5 carbon atoms and $NR^2R$ is a group $-NH.CO.NHR^4$ or $-NH.CS.NHR^4$, wherein $R^4$ is selected from unsubstituted or substituted phenyl, pyrid-2-yl, pyrid-3-yl and pyrid-4-yl groups.

* * * * *

UNITED STATES PATENT AND TRADEMARK OFFICE
CERTIFICATE OF CORRECTION

PATENT NO.  :  4,837,234                                    Page 1 of 3
DATED       :  June 6, 1989
INVENTOR(S) :  JONES et al It is certified that error appears in the above-identified patent and that said Letters Patent is hereby corrected as shown below:

Column 8 line 65 delete "right" and replace by --ring--

Column 13 line 60 insert --$R^1$-- before "as"

Column 13 line 60 delete "R'"

Column 14 lines 67 and 68 delete and replace by the following:

--(-CHOH-$CH_2NO_2$ → -CH=$CHNO_2$ → -$CH_2CH_2NO_2$) or using acetic anhydride with N,N-dime- --

Column 15 lines 2 and 3 delete and replace by the following:

--borohydride reduction (-CHOH-$CH_2NO_2$ → -CHOAc-$CH_2NO_2$ → -$CH_2CH_2NO_2$). A Nef reac- --

Column 15 lines 4 and 5 delete and replace by the following:

--tion may then be employed to produce a group -$CH_2$-CHO or -CR'''-CHO. Thus for example, sodium--

Column 15 lines 9 and 10 cancel and replace by the following:

--hydrochloric acid in chloroform to give a group -$CH_2$-CHO.--

Column 15 line 53 delete "barohydride" and replace by --borohydride--

Column 27 line 9 delete "(1) assignment not fully clear."

UNITED STATES PATENT AND TRADEMARK OFFICE
CERTIFICATE OF CORRECTION

PATENT NO. : 4,837,234    Page 2 of 3

DATED : June 6, 1989

INVENTOR(S) : JONES et al

It is certified that error appears in the above-identified patent and that said Letters Patent is hereby corrected as shown below:

Column 28 Table 5 heading of right hand column amend to read as follows:

--NH and OH protons $-A-N\underline{H}CBN\underline{H}R^4-CO_2H$ --

Column 30 line 17 delete the three bicyclic ring systems

Column 30 line 25 delete the extreme left hand 7-oxa-bicyclo heptene ring system Column 31 line 19 insert --,-- after "$-CNH.NR^3R^4$"

Column 31 line 20 delete "A" and replace by --a--

Column 31 line 20 delete "$CO.R^4$" and replace by --$CO.R^4$--

Column 31 line 21 delete "AR" and replace by --Ar--

Column 31 line 22 delete in its entirety

Column 32 line 1 delete "$-CH(CH_3)CH_3-$" and replace by $-CH(CH_3)CH_2-$ --

Column 32 line 61 delete "of" and replace by --or--

UNITED STATES PATENT AND TRADEMARK OFFICE
CERTIFICATE OF CORRECTION

PATENT NO. : 4,837,234

DATED : June 6, 1989

INVENTOR(S) : JONES et al

It is certified that error appears in the above-identified patent and that said Letters Patent is hereby corrected as shown below:

Column 30 line 32 delete the bicyclic ring system on the extreme right and replace by the following:

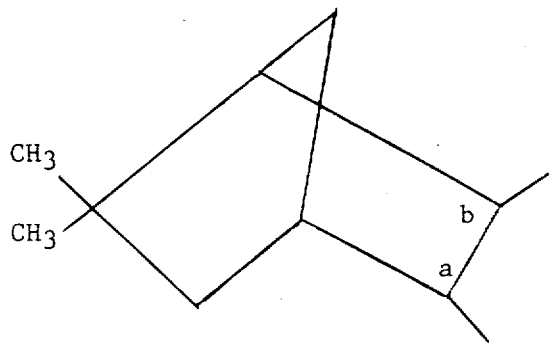

Signed and Sealed this

Twentieth Day of August, 1991

Attest:

HARRY F. MANBECK, JR.

Attesting Officer

Commissioner of Patents and Trademarks